(12) United States Patent
Olson et al.

(10) Patent No.: US 7,938,851 B2
(45) Date of Patent: May 10, 2011

(54) DEVICES AND METHODS FOR OPERATING AND CONTROLLING INTERVENTIONAL APPARATUS

(75) Inventors: Stephen Lee Olson, Los Altos, CA (US); Michael C. McGarry, Truckee, CA (US)

(73) Assignee: XTENT, Inc., Los Altos, CA (US)

( * ) Notice: Subject to any disclaimer, the term of this patent is extended or adjusted under 35 U.S.C. 154(b) by 627 days.

(21) Appl. No.: 11/148,713

(22) Filed: Jun. 8, 2005

(65) Prior Publication Data

US 2006/0282150 A1  Dec. 14, 2006

(51) Int. Cl.
*A61F 2/06* (2006.01)
(52) U.S. Cl. ....................................................... 623/1.11
(58) Field of Classification Search .................. 606/1.11, 606/1.12, 108; 604/95.01, 528; 623/1.11, 623/1.12
See application file for complete search history.

(56) References Cited

U.S. PATENT DOCUMENTS

| | | | |
|---|---|---|---|
| 3,173,418 A | 3/1965 | Baran | |
| 3,394,075 A | 7/1968 | Abramson | |
| 3,938,502 A | 2/1976 | Bom | |
| 4,292,974 A | 10/1981 | Fogarty et al. | |
| 4,323,071 A | 4/1982 | Simpson et al. | |
| 4,327,721 A | 5/1982 | Goldin et al. | |
| 4,406,656 A | 9/1983 | Hattler et al. | |
| 4,417,576 A | 11/1983 | Barab | |
| 4,437,856 A | 3/1984 | Valli | |
| 4,564,014 A | 1/1986 | Fogarty et al. | |
| 4,576,177 A | 3/1986 | Webster, Jr. | |
| 4,580,568 A | 4/1986 | Gianturci | |
| 4,661,094 A | 4/1987 | Simpson | |
| 4,665,918 A | 5/1987 | Garza et al. | |
| 4,681,110 A | 7/1987 | Wiktor | |
| 4,681,564 A | 7/1987 | Landreneau | |
| 4,693,243 A | 9/1987 | Buras | |
| 4,731,049 A | 3/1988 | Parsi | |
| 4,733,665 A | 3/1988 | Palmz | |

(Continued)

FOREIGN PATENT DOCUMENTS

EP  274129 B1  7/1988

(Continued)

OTHER PUBLICATIONS

Born, N. et al."Early and recent intraluminal ultrasound devices," 1989, Internal Journal of Cardiac Imaging 4:79-88.

(Continued)

*Primary Examiner* — (Jackie) Tan-Uyen T Ho
*Assistant Examiner* — Thomas McEvoy
(74) *Attorney, Agent, or Firm* — Levine Bagade Han LLP

(57) ABSTRACT

Devices and methods are provided for operating and controlling an interventional element on an interventional catheter. The interventional element may be a stent or series of stents, a balloon, or any other interventional element for which length control is necessary or desirable. A handle member includes an elongated body and an actuator knob that rotates around the longitudinal axis of the body. Rotational movement of the actuator knob is translated to rotational movement of one or more lead screws by a system of gears, rollers, or combinations of gears and rollers. Each of one or more axially moveable members is positioned on a lead screw and attached to a portion of the catheter shaft in order to provide the ability to advance or retract the portion of the catheter shaft.

7 Claims, 17 Drawing Sheets

U.S. PATENT DOCUMENTS

| | | |
|---|---|---|
| 4,739,762 A | 4/1988 | Palmz |
| 4,744,790 A | 5/1988 | Jankowski et al. |
| 4,762,129 A | 8/1988 | Bonzel |
| 4,775,337 A | 10/1988 | Van Wagener et al. |
| 4,775,371 A | 10/1988 | Mueller, Jr. |
| 4,776,337 A | 10/1988 | Palmz |
| 4,790,315 A | 12/1988 | Mueller, Jr. et al. |
| 4,839,623 A | 6/1989 | Schonstedt et al. |
| 4,841,977 A | 6/1989 | Griffith et al. |
| 4,850,358 A | 7/1989 | Millar |
| 4,850,969 A | 7/1989 | Jackson |
| 4,877,030 A | 10/1989 | Beck et al. |
| 4,877,031 A | 10/1989 | Conway et al. |
| 4,886,062 A | 12/1989 | Wiktor |
| 4,892,519 A | 1/1990 | Songer et al. |
| 4,911,163 A | 3/1990 | Fina |
| 4,917,097 A | 4/1990 | Proudian et al. |
| 4,950,227 A | 8/1990 | Savin et al. |
| 4,950,232 A | 8/1990 | Ruzicka et al. |
| 4,976,689 A | 12/1990 | Buchbinder et al. |
| 4,988,356 A | 1/1991 | Crittenden et al. |
| 4,994,033 A | 2/1991 | Shockey et al. |
| 4,994,066 A | 2/1991 | Voss |
| 4,994,069 A | 2/1991 | Ritchart et al. |
| 5,000,734 A | 3/1991 | Boussignac et al. |
| 5,007,897 A | 4/1991 | Kalb et al. |
| 5,009,636 A | 4/1991 | Wortley et al. |
| 5,014,089 A | 5/1991 | Sakashita et al. |
| 5,015,232 A | 5/1991 | Maglinte |
| 5,019,042 A | 5/1991 | Sahota |
| 5,019,090 A | 5/1991 | Pinchuk |
| 5,021,044 A | 6/1991 | Sharkawy |
| 5,026,377 A | 6/1991 | Burton et al. |
| 5,034,001 A | 7/1991 | Garrison et al. |
| 5,041,089 A | 8/1991 | Mueller et al. |
| 5,046,497 A | 9/1991 | Millar |
| 5,049,132 A | 9/1991 | Shaffer et al. |
| 5,087,244 A | 2/1992 | Wolinsky et al. |
| 5,087,247 A | 2/1992 | Horn et al. |
| 5,092,877 A | 3/1992 | Pinchuk |
| 5,102,390 A | 4/1992 | Crittenden et al. |
| 5,102,415 A | 4/1992 | Guenther et al. |
| 5,102,417 A | 4/1992 | Palmz |
| 5,104,404 A | 4/1992 | Wolff |
| 5,108,416 A | 4/1992 | Ryan et al. |
| 5,112,303 A | 5/1992 | Pudenz et al. |
| 5,112,305 A | 5/1992 | Barath et al. |
| 5,123,917 A | 6/1992 | Lee |
| 5,135,535 A | 8/1992 | Kramer |
| 5,158,548 A | 10/1992 | Lau et al. |
| 5,163,921 A | 11/1992 | Feiring |
| 5,163,952 A | 11/1992 | Froix |
| 5,180,364 A | 1/1993 | Ginsburg |
| 5,180,366 A | 1/1993 | Woods |
| 5,180,368 A | 1/1993 | Garrison |
| 5,192,307 A | 3/1993 | Wall |
| 5,195,984 A | 3/1993 | Schatz |
| 5,203,338 A | 4/1993 | Jang |
| 5,213,576 A | 5/1993 | Abiuso et al. |
| 5,217,495 A | 6/1993 | Kaplan et al. |
| 5,219,326 A | 6/1993 | Hattler |
| 5,219,335 A | 6/1993 | Willard et al. |
| 5,219,355 A | 6/1993 | Parodi et al. |
| 5,226,888 A | 7/1993 | Arney |
| 5,226,913 A | 7/1993 | Pinchuk |
| 5,242,396 A | 9/1993 | Evard |
| 5,242,399 A | 9/1993 | Lau et al. |
| 5,242,451 A | 9/1993 | Harada et al. |
| 5,246,421 A | 9/1993 | Saab |
| 5,254,089 A | 10/1993 | Wang |
| 5,257,974 A | 11/1993 | Cox |
| 5,266,073 A | 11/1993 | Wall |
| 5,273,536 A | 12/1993 | Savas |
| 5,281,200 A | 1/1994 | Corso, Jr. et al. |
| 5,282,785 A | 2/1994 | Shapland et al. |
| 5,284,473 A | 2/1994 | Calabria |
| 5,295,962 A | 3/1994 | Crocker et al. |
| 5,300,085 A | 4/1994 | Yock |
| 5,306,250 A | 4/1994 | March et al. |
| 5,308,356 A | 5/1994 | Blackshear, Jr. et al. |
| 5,318,535 A | 6/1994 | Miraki |
| 5,334,187 A | 8/1994 | Fischell et al. |
| 5,344,401 A | 9/1994 | Radisch et al. |
| 5,344,426 A | 9/1994 | Lau et al. |
| 5,358,487 A | 10/1994 | Miller |
| 5,360,401 A | 11/1994 | Turnland et al. |
| 5,360,443 A | 11/1994 | Barone et al. |
| 5,364,356 A | 11/1994 | Hofling |
| 5,370,617 A | 12/1994 | Sahota |
| 5,378,237 A | 1/1995 | Boussignac et al. |
| 5,382,261 A | 1/1995 | Palmz |
| 5,395,333 A | 3/1995 | Brill |
| 5,409,495 A | 4/1995 | Osborn |
| 5,411,507 A | 5/1995 | Heckele |
| 5,415,637 A | 5/1995 | Khosravi |
| 5,421,955 A | 6/1995 | Lau et al. |
| 5,425,709 A | 6/1995 | Gambale |
| 5,433,706 A | 7/1995 | Abiuso |
| 5,439,445 A | 8/1995 | Kontos |
| 5,443,500 A | 8/1995 | Sigwart |
| 5,445,646 A | 8/1995 | Euteneuer et al. |
| 5,478,349 A | 12/1995 | Nicholas |
| 5,501,227 A | 3/1996 | Yock |
| 5,507,768 A | 4/1996 | Lau et al. |
| 5,507,771 A | 4/1996 | Gianturco |
| 5,514,093 A | 5/1996 | Ellis et al. |
| 5,514,154 A | 5/1996 | Lau et al. |
| 5,527,354 A | 6/1996 | Fontaine et al. |
| 5,534,007 A | 7/1996 | St. Germain et al. |
| 5,545,209 A | 8/1996 | Roberts et al. |
| 5,549,551 A | 8/1996 | Peacock et al. |
| 5,549,563 A | 8/1996 | Kronner |
| 5,549,635 A | 8/1996 | Solar |
| 5,554,181 A | 9/1996 | Das |
| 5,562,725 A | 10/1996 | Schmitt et al. |
| 5,571,086 A | 11/1996 | Kaplan et al. |
| 5,591,222 A | 1/1997 | Susawa et al. |
| 5,607,463 A | 3/1997 | Schwartz et al. |
| 5,620,457 A | 4/1997 | Pinchasik et al. |
| 5,628,775 A | 5/1997 | Jackson et al. |
| 5,634,928 A | 6/1997 | Fischell et al. |
| 5,676,654 A | 10/1997 | Ellis et al. |
| 5,683,451 A | 11/1997 | Lenker et al. |
| 5,697,948 A | 12/1997 | Marin et al. |
| 5,722,669 A | 3/1998 | Shimizu et al. |
| 5,735,869 A | 4/1998 | Fernandez-Aceytuno |
| 5,749,848 A | 5/1998 | Jang et al. |
| 5,755,772 A | 5/1998 | Evans et al. |
| 5,755,776 A | 5/1998 | Al-Saadon |
| 5,755,781 A | 5/1998 | Jayaraman |
| 5,769,882 A | 6/1998 | Fogarty et al. |
| 5,772,669 A | 6/1998 | Vrba |
| 5,776,141 A | 7/1998 | Klein et al. |
| 5,807,398 A | 9/1998 | Shaknovich |
| 5,824,040 A | 10/1998 | Cox et al. |
| 5,824,041 A | 10/1998 | Lenker et al. |
| 5,833,694 A | 11/1998 | Poncet |
| 5,836,964 A | 11/1998 | Richter et al. |
| 5,843,092 A | 12/1998 | Heller et al. |
| 5,858,556 A | 1/1999 | Eckert et al. |
| 5,870,381 A | 2/1999 | Kawasaki et al. |
| 5,879,370 A | 3/1999 | Fischell et al. |
| 5,891,190 A | 4/1999 | Boneau |
| 5,895,398 A | 4/1999 | Wensel et al. |
| 5,902,332 A | 5/1999 | Schatz |
| 5,961,536 A | 10/1999 | Mickley et al. |
| 5,976,155 A | 11/1999 | Foreman et al. |
| 5,980,484 A | 11/1999 | Ressemann et al. |
| 5,980,486 A | 11/1999 | Enger |
| 5,980,552 A | 11/1999 | Pinchasik et al. |
| 5,984,957 A | 11/1999 | Laptewicz, Jr. et al. |
| 5,993,466 A * | 11/1999 | Yoon ............................ 606/147 |
| 6,007,517 A | 12/1999 | Anderson |
| 6,022,359 A | 2/2000 | Frantzen |
| 6,033,434 A | 3/2000 | Borghi |
| 6,056,722 A | 5/2000 | Jayaraman |
| 6,066,155 A | 5/2000 | Amann et al. |

| | | | |
|---|---|---|---|
| 6,068,655 A | 5/2000 | Seguin et al. | |
| 6,090,063 A | 7/2000 | Makower et al. | |
| 6,090,136 A | 7/2000 | McDonald et al. | |
| 6,106,530 A | 8/2000 | Harada | |
| RE36,857 E | 9/2000 | Euteneuer et al. | |
| 6,126,685 A | 10/2000 | Lenker et al. | |
| 6,143,016 A | 11/2000 | Bleam et al. | |
| 6,165,167 A | 12/2000 | Delaloye | |
| 6,179,878 B1 | 1/2001 | Duering | |
| 6,187,034 B1 | 2/2001 | Frantzen | |
| 6,190,402 B1 | 2/2001 | Horton et al. | |
| 6,196,995 B1 | 3/2001 | Fagan | |
| 6,200,337 B1 | 3/2001 | Moriuchi et al. | |
| 6,203,550 B1 * | 3/2001 | Olson | 606/108 |
| 6,241,691 B1 | 6/2001 | Ferrera et al. | |
| 6,251,132 B1 | 6/2001 | Ravenscroft et al. | |
| 6,251,134 B1 | 6/2001 | Alt et al. | |
| 6,254,628 B1 | 7/2001 | Wallace et al. | |
| 6,258,117 B1 | 7/2001 | Camrud et al. | |
| 6,273,913 B1 | 8/2001 | Wright et al. | |
| 6,312,458 B1 | 11/2001 | Golds | |
| 6,315,794 B1 | 11/2001 | Richter | |
| 6,319,227 B1 | 11/2001 | Mansouri-Ruiz | |
| 6,319,277 B1 | 11/2001 | Rudnick et al. | |
| 6,357,104 B1 | 3/2002 | Myers | |
| 6,375,676 B1 | 4/2002 | Cox | |
| 6,383,171 B1 | 5/2002 | Gifford et al. | |
| 6,419,693 B1 | 7/2002 | Fariabi | |
| 6,451,025 B1 | 9/2002 | Jervis | |
| 6,451,050 B1 | 9/2002 | Rudakov et al. | |
| 6,468,298 B1 | 10/2002 | Pelton | |
| 6,468,299 B2 | 10/2002 | Stack et al. | |
| 6,485,510 B1 | 11/2002 | Camrud et al. | |
| 6,488,694 B1 | 12/2002 | Lau et al. | |
| 6,511,468 B1 | 1/2003 | Cragg et al. | |
| 6,520,987 B1 | 2/2003 | Plante | |
| 6,527,789 B1 | 3/2003 | Lau et al. | |
| 6,527,799 B2 | 3/2003 | Shanley | |
| 6,555,157 B1 | 4/2003 | Hossainy | |
| 6,575,993 B1 | 6/2003 | Yock | |
| 6,582,394 B1 | 6/2003 | Reiss et al. | |
| 6,592,549 B2 | 7/2003 | Gerdts et al. | |
| 6,605,062 B1 | 8/2003 | Hurley et al. | |
| 6,645,547 B1 | 11/2003 | Shekalim et al. | |
| 6,656,212 B2 | 12/2003 | Ravenscroft et al. | |
| 6,666,883 B1 | 12/2003 | Sequin et al. | |
| 6,679,909 B2 | 1/2004 | McIntosh et al. | |
| 6,692,465 B2 | 2/2004 | Kramer | |
| 6,702,843 B1 | 3/2004 | Brown | |
| 6,712,827 B2 | 3/2004 | Ellis et al. | |
| 6,712,845 B2 | 3/2004 | Hossainy | |
| 6,723,071 B2 | 4/2004 | Gerdts et al. | |
| 6,743,251 B1 | 6/2004 | Eder | |
| 6,866,669 B2 | 3/2005 | Buzzard et al. | |
| 6,884,257 B1 | 4/2005 | Cox | |
| 2001/0020181 A1 | 9/2001 | Layne | |
| 2001/0044595 A1 | 11/2001 | Reydel et al. | |
| 2002/0049415 A1 * | 4/2002 | Fukuda | 604/191 |
| 2002/0072704 A1 * | 6/2002 | Mansouri-Ruiz | 604/95.01 |
| 2002/0138132 A1 | 9/2002 | Brown | |
| 2002/0151955 A1 | 10/2002 | Tran et al. | |
| 2002/0156496 A1 | 10/2002 | Chermoni | |
| 2002/0188343 A1 | 12/2002 | Mathis | |
| 2002/0188347 A1 | 12/2002 | Mathis | |
| 2003/0045923 A1 | 3/2003 | Bashiri et al. | |
| 2003/0114919 A1 | 6/2003 | McQuiston et al. | |
| 2003/0114922 A1 | 6/2003 | Iwasaka et al. | |
| 2003/0139796 A1 | 7/2003 | Sequin et al. | |
| 2003/0139797 A1 | 7/2003 | Johnson et al. | |
| 2003/0176909 A1 | 9/2003 | Kusleika | |
| 2003/0199821 A1 | 10/2003 | Gerdts et al. | |
| 2004/0087965 A1 | 5/2004 | Levine et al. | |
| 2004/0098081 A1 * | 5/2004 | Landreville et al. | 623/1.11 |
| 2004/0167511 A1 * | 8/2004 | Buehlmann et al. | 606/45 |
| 2005/0033402 A1 * | 2/2005 | Cully et al. | 623/1.11 |
| 2005/0240254 A1 * | 10/2005 | Austin | 623/1.11 |
| 2006/0184124 A1 * | 8/2006 | Cowan et al. | 604/155 |

FOREIGN PATENT DOCUMENTS

| | | |
|---|---|---|
| EP | 282143 | 9/1988 |
| EP | 533960 | 3/1993 |
| EP | 203945 B2 | 12/1996 |
| WO | WO 87/07510 | 12/1987 |
| WO | WO 88/09682 | 12/1988 |
| WO | WO 92/11890 | 7/1992 |
| WO | WO 92/11895 | 7/1992 |
| WO | WO 93/21985 | 11/1993 |
| WO | WO 94/11048 | 5/1994 |
| WO | WO 94/11053 | 5/1994 |
| WO | WO 95/03081 | 2/1995 |
| WO | WO 95/03082 | 2/1995 |
| WO | WO 95/11055 | 4/1995 |
| WO | WO 96/33677 | 10/1996 |
| WO | WO 97/46174 | 12/1997 |
| WO | WO 99/01087 A1 | 1/1999 |
| WO | WO 00/15151 A1 | 3/2000 |
| WO | WO 00/32136 A1 | 6/2000 |
| WO | WO 00/41649 A1 | 7/2000 |
| WO | WO 01/91918 | 12/2001 |
| WO | WO 03/022178 A1 | 3/2003 |
| WO | WO 03/051425 | 6/2003 |
| WO | WO 2004/017865 | 3/2004 |
| WO | WO 2004/043299 | 5/2004 |
| WO | WO 2004/043301 | 5/2004 |
| WO | WO 2004/043510 | 5/2004 |
| WO | WO 2004/052237 | 6/2004 |

OTHER PUBLICATIONS

Cooley et al., "Applications of Ink-Jet Printing Technology to BioMEMs and Microfluidic Systems," Proceedings, SPIE Conference on Microfluidics and BioMEMs, (Oct. 2001).

Hong, M. K. et al. "A New PTCA Balloon Catheter With Intramural Channels For Local Delivery of Drugs at Low Pressure," 1992, Supplement to Circulation, Abstracts From the 65th Scientific Sessions, vol. 86, No. 4, #1514.

Stimpson et al, Parallel Production of Oligonucleotide Arrays Using Membranes and Reagent Jet Printing, BioTechniques 25:886-890 (Nov. 1998).

* cited by examiner

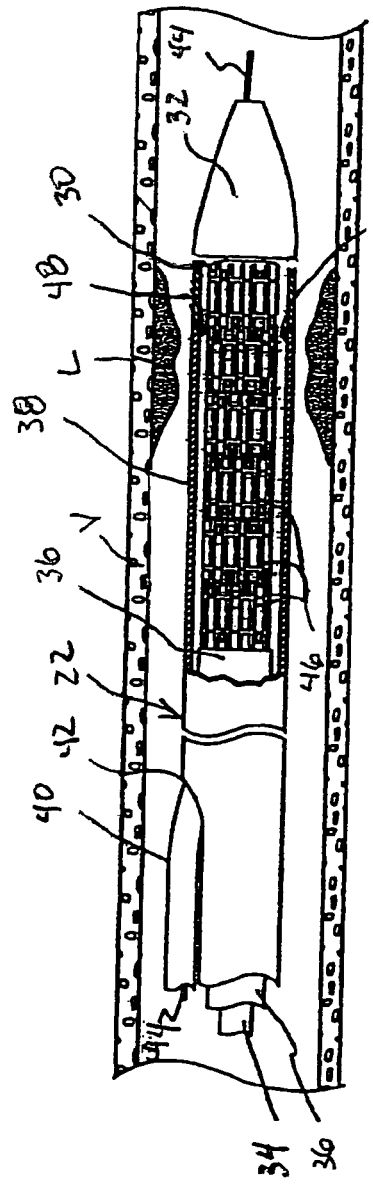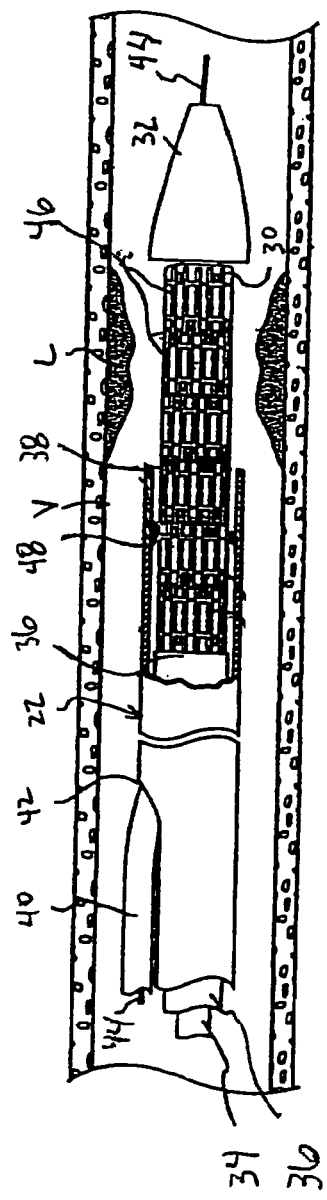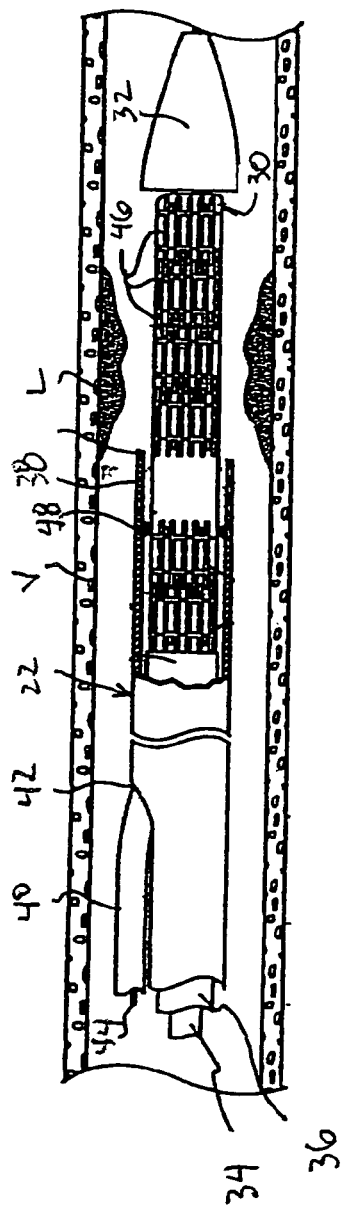

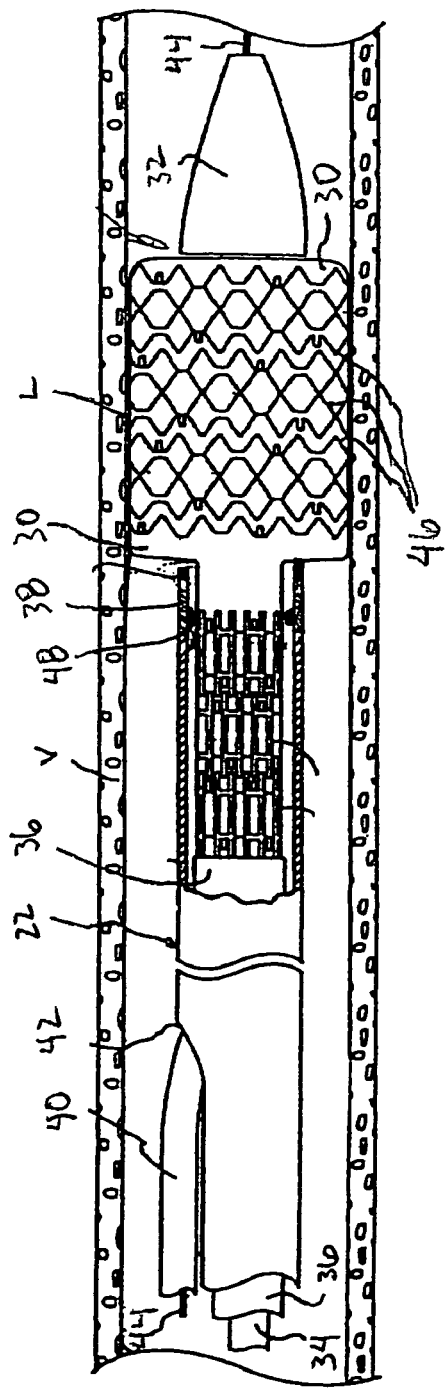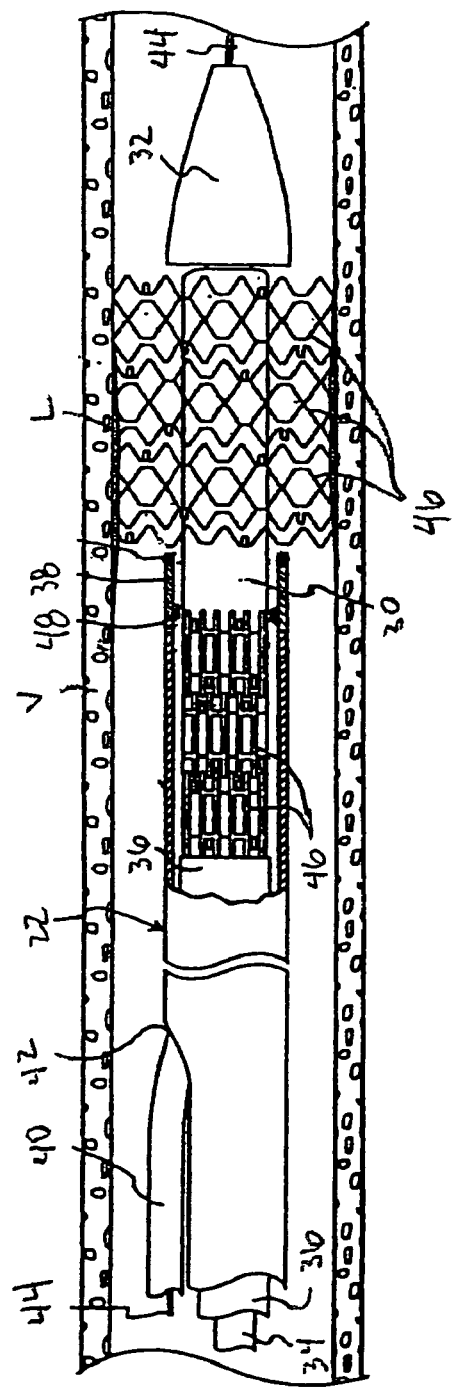
FIG. 11E
FIG. 11D

DEVICES AND METHODS FOR OPERATING AND CONTROLLING INTERVENTIONAL APPARATUS

FIELD OF THE INVENTION

The present invention relates generally to interventional catheters and prostheses, and more specifically to catheters and prostheses for treatment of vascular diseases, including coronary artery disease and peripheral vascular disease, as well as diseases of other body lumens such as the biliary tract, fallopian tubes, urinary and digestive tracts, and other structures.

BACKGROUND OF THE INVENTION

Balloon angioplasty and stenting are widely used in the treatment of coronary artery disease and peripheral vascular disease. In coronary artery disease, one or more coronary blood vessels become narrowed or closed due to the buildup of stenotic plaques on the arterial wall. This blocks blood flow to the heart muscle, potentially causing myocardial infarction. Such narrowing can also occur in peripheral blood vessels such as the carotids, femorals, iliacs and other arteries, blocking blood supply to other vital tissues and organs.

Balloon angioplasty involves the use of a long flexible catheter having a balloon at its distal tip. The catheter is inserted into a peripheral artery such as the femoral and advanced transluminally into the diseased artery. The balloon is inflated within the narrowed portion of the vessel, thereby expanding the vascular lumen and restoring normal blood flow.

In some cases, however, balloon angioplasty alone is inadequate to treat vascular disease due to restenosis, the renarrowing of the artery following angioplasty. Stents have been developed to provide an intravascular frame or scaffold to maintain patency of the vascular lumen after it has been expanded. Stents are small tubular prostheses designed to be advanced to the treatment site in a collapsed configuration using an elongated delivery catheter. The stents are then expanded at the treatment site into engagement with the vessel wall to maintain vascular patency.

Stents may be either self-expanding or balloon expandable. Self-expanding stents are made of a shape memory material such as Nitinol and can be delivered in a compressed state within the tip of the delivery catheter and allowed to resiliently expand upon release from the delivery catheter. Balloon expandable stents are made of a malleable metal and are mounted to a balloon on the delivery catheter. When positioned at the treatment site, the balloon in inflated to expand the stent into engagement with the vessel.

Stents, however, have also suffered from the problem of restenosis. Restenosis rates with conventional coronary stents have ranged from 30-40%. The causes of such restenosis are not fully understood. However, it is believed that restenosis may be caused in some cases by the excessive stiffness of current stents and their inability to conform to vascular curves, shapes, dimensional changes, and movements. This problem is particularly acute with longer lesions, which may extend over curved and tapered sections of a vessel and may be subject to non-uniform movements along their lengths.

The need has thus been demonstrated for highly-flexible stents that may be used to treat long, curved, and tapered vascular regions. In co-pending U.S. patent application Ser. No. 10/637,713, filed Aug. 8, 2003, entitled "Apparatus and Methods for Delivery of Vascular Prostheses, the full disclosure of which is incorporated herein by reference, highly flexible multi-segmented stents and associated delivery devices are disclosed that enable the treatment of long, curved or tapered vascular lesions. The disclosed delivery devices enable the selective deployment of one or more stent segments at a treatment site to allow the user to customize stent length in situ. Moreover, the device can be repositioned at multiple vascular sites to deploy a plurality of stents at various lengths.

Other custom-length stents and delivery devices are described in co-pending U.S. patent application Ser. No. 10/624,451, filed Jul. 21, 2003, entitled "Apparatus and Methods for Delivery of Multiple Distributed Stents," which is also incorporated herein by reference. This application describes separable stent segments as well as continuous prosthesis structures configured as braids or coils that allow the user to pay out a selected length of the prosthesis structure and deploy it into the vessel at one or more treatment sites.

Variable length angioplasty devices have also been proposed. For example, U.S. Pat. No. 5,246,421 to Saab discloses angioplasty catheters having an elongated balloon and an external sheath that is axially slidable relative to the balloon. The sheath can be retracted to expose a selected length of the balloon for expansion at a treatment site. The catheter can then be repositioned and another length of balloon exposed to treat one or more additional sites.

The need has thus also been demonstrated for improved ways of controlling and providing indication of balloon and stent length in angioplasty and stenting catheters and other devices. In co-pending U.S. patent application Ser. No. 10/746,466, filed Dec. 23, 2003, entitled "Devices and Methods for Controlling and Indicating the Length of an Interventional Element," the full disclosure of which is incorporated herein by reference, devices and methods are disclosed that control an interventional element through the use of gear driven actuators, motors, and other mechanisms. The disclosed devices provide an indication to the user of the length of an interventional element by the use of sensors, detents, visual displays and other mechanisms that provide visual, audible, and tangible indications of length to the user. The disclosed control and indication devices preferably operate in tandem to enable highly precise adjustment of interventional element length.

While such custom-length stents, angioplasty catheters, and controlling and indicating devices have shown great promise, there remains a need for improved ways of controlling and operating interventional apparatus such as angioplasty and stenting catheters.

SUMMARY OF THE INVENTION

The invention provides devices and methods for operating and controlling interventional apparatus, primarily those apparatus used in minimally invasive surgical procedures. The devices and methods facilitate accurate control of the interventional apparatus, including control of the working or deployed length of an interventional element being deployed by the apparatus. The types of interventional elements to which the invention may be applied are many, but in preferred embodiments include stents and balloons for the treatment of vascular disease.

In a first aspect, an interventional catheter comprises an elongated flexible shaft having a distal end and a proximal end, and an interventional element at the distal end, the interventional element having an adjustable length. An actuator is disposed near the proximal end for adjusting the length of the interventional element. In exemplary embodiments, the interventional element comprises a balloon. A sheath is movably disposed over the balloon and the actuator is coupled to the sheath to axially position the sheath relative to the balloon. In this way the sheath may be used to selectively cover part of the balloon while exposing part of the balloon having a desired length, the sheath constraining the covered part from expansion.

In other embodiments, the interventional element comprises a stent releasably carried by the shaft. The actuator controls the length of a deployable portion of the stent, the deployable portion being released from the shaft while an undeployed portion of the stent remains associated with the shaft. The actuator may be coupled to a sheath that may be axially positioned to cover a first portion of the stent while a second portion of the stent having a desired length is left uncovered for deployment. The stent may be either balloon expandable or self-expanding. In a preferred embodiment, the stent is comprised of a plurality of separable stent segments and stent length is controlled by exposing a desired number of stent segments outside of the sheath.

The elongated catheter shaft may include an outer sheath and an inner shaft. The outer sheath is preferably slidably disposed over the inner shaft. The inner shaft may include an inflation lumen that provides fluid communication between a proximal end of the catheter shaft and the distal end of the catheter shaft. An optional intermediate shaft may be included, with the intermediate shaft being slidably disposed over the inner shaft and within the outer sheath. In those embodiments that include a stent or stent segments, the intermediate shaft may serve as a pusher to selectively engage the stent or stent segments. Additional intermediate shafts may also be provided where additional finctionality is desired.

In another aspect, a handle for controlling the operation of a catheter includes a body having a longitudinal axis, and an actuator knob that is preferably rotatable around the longitudinal axis. Rotation of the actuator knob is translated to rotational movement of one or more lead screws oriented longitudinally within the body of the handle member. In some embodiments, one or more gear systems are used to provide the translation. A first gear system may be interposed between the actuator knob and a first lead screw such that, when the first gear system is engaged, rotation of the actuator knob causes rotation of the first lead screw. Similarly, a second gear system may be interposed between the actuator knob and a second lead screw such that, when the second gear system is engaged, rotation of the actuator knob causes rotation of the second lead screw. Additional gear systems may be included to drive additional lead screws in certain embodiments. Preferably, one, more than one, or all of the gear systems are selectively disengageable such that rotation of the actuator knob does not cause rotation of the respective lead screw.

In other embodiments, a system of rollers and actuator knob engagement surfaces provides the translation of rotation of the actuator knob to rotational movement of the one or more lead screws. Each roller is selectively engageable with one or more engagement surfaces of the actuator knob such that rotation of the actuator knob causes the roller to rotate. Each roller may be directly or indirectly connected to a respective lead screw to cause the lead screw to rotate as the roller rotates. In a preferred embodiment, the rotation direction of a roller may be different dependent upon the actuator knob engagement surface the roller is engaged with, thereby providing the capability to reverse the rotation of the lead screw for a given rotation direction of the actuator knob.

At least one threaded engagement member, such as a nut, may be movably engaged to each of the lead screws such that rotation of the lead screw produces axial movement of the engagement member. Each of the at least one engagement members may be attached, in turn, to one of the outer sheath, the intermediate shaft, the inner shaft, or any other shaft included in the catheter body to provide selective independent or simultaneous advancement or retraction of each of those shafts.

A selector member may be provided to selectively engage or disengage one or more of the lead screws, such as by engaging and disengaging the gear or roller systems interposed between the actuator knob and the lead screws. The selector member preferably is a rotatable member that rotates around the longitudinal axis of the handle. Preferably, the selector and the actuator knob are provided on the handle in an orientation that allows the user to hold the handle, to switch the selector, and to rotate the actuator knob using only a single hand. The selector is positionable to one or more settings, with each setting corresponding to a separate mode of action of the actuator. In a first mode of action, a first one of the lead screws is engaged to the actuator knob such that rotation of the actuator knob causes rotation of the first lead screw. In a second mode of action, a second one of the lead screws is engaged to the actuator knob such that rotation of the actuator knob causes rotation of the second lead screw. Preferably, the first lead screw is also engaged to the actuator knob during the second mode of action, although the selector may be configured to disengage the first lead screw during the second mode of action if desired. In those embodiments in which the actuator includes more than two lead screws, the selector may be provided with third, fourth, or additional settings to correspond with a desired mode of action, with each setting corresponding with one or more lead screws being engaged to the actuator knob.

The selector member preferably is generally disc-shaped. In some embodiments, the selector is provided with one or more ramps on a distal-facing or proximal-facing surface that are adapted to engage and displace a gear advancer as the selector member is rotated. Alternatively, the ramps may be located on the gear advancer, or on both the selector member and the gear advancer. The gear advancer then engages a gear member to cause the gear member to engage a drive gear and operatively couple the actuator knob with a lead screw. In other embodiments, the selector is provided with one or more slots having a cammed surface through which a roller extends. The roller is thereby radially displaced by the cammed surface as the selector is rotated, causing the roller to engage or disengage with an engagement surface of the actuator knob, thereby selectively coupling the actuator knob with a lead screw.

The handle may be provided with an optional lock-out mechanism that selectively prevents the actuator knob from rotating one or more of the lead screws when the selector member is in a predetermined position corresponding to a predetermined mode of operation. The preferred lock-out mechanism includes a rocker arm having a pawl formed on one end thereof, the pawl being selectively engageable with a gear interposed between the actuator knob and a lead screw. A pin selectively engages the rocker arm to cause the pawl to engage or disengage from the gear. When the pawl is engaged, the gear is only allowed to rotate in an allowed direction, but is prevented from rotating in the opposite direction. The lock-out mechanism may be used, for example, to prevent advancement of the outer sheath when the actuator is in a mode of operation corresponding with inflation of the balloon at the distal end of the catheter. Other uses of the lock-out mechanism are also possible.

The handle may also be provided with an optional clutch mechanism that causes the actuator knob to become disengaged from the drive shaft when a predetermined amount of torque is applied to the actuator knob. The clutch mechanism includes a first clutch plate attached to the actuator knob, and a second clutch plate attached to the drive shaft. The drive shaft, in turn, is selectively coupled to the one or more lead screws. Under normal operation, with the clutch engaged, rotation of the actuator knob causes rotation of the one or more lead screws (when engaged by the selector). However, the clutch plates are constructed such that, when the amount of torque applied to the actuator knob reaches a predetermined limit, the clutch plates disengage, thereby preventing the actuator knob from causing rotation of any of the one or more lead screws. Selected clutch disengagement may be obtained by appropriate construction of the clutch plate teeth, by selection of materials, by selection of a clutch spring of appropriate size and spring constant, or by other methods known in the art. The clutch mechanism may be useful, for example, to prevent over-resetting the outer sheath when the sheath is being advanced distally.

The handle may also be provided with an optional inflation lumen disable mechanism that prevents the user from supplying fluid to the distal end of the catheter shaft via the inflation lumen during certain modes of operation of the handle. The inflation lumen disable mechanism may include an electronic or mechanical valve that is placed in the inflation lumen line and that is switchable from a first position allowing fluid flow to a second position preventing fluid flow.

Alternatively, the inflation lumen disable mechanism may include a clamp that is applied to a portion of tubing or other member placed in the inflation lumen line. Either mechanism may be used to substantially or completely prevent or divert fluid flow away from or out of the inflation lumen.

The handle may also be provided with a limiting mechanism that limits the amount of axial movement of one or more of the threaded engagement members on the respective lead screws. For example, a tab may be fixed to a surface of an engagement member such that it engages a detent formed on an internal surface of the handle housing when the engagement member reaches a predetermined point of travel along the lead screw. The detent engages the tab, preventing any further axial movement of the engagement member. In some embodiments, the position of the detent within the handle housing is adjustable, thereby providing the user with the capability of adjusting the length of allowable travel of the engagement member.

Additional features that optionally may be included on or with the handle include the use of one or more variable pitch lead screws to provide the ability to speed up or slow down the axial movement of the engagement member on the lead screw for a given rotation speed. Thus, certain modes of operation may be performed more quickly, while other modes of operation (e.g., those that require fine adjustment) may be performed more slowly. Yet another additional option feature is the provision of a motor either internally or externally of the handle, the motor being adapted to automate or semi-automate the handle operation. The motor may optionally be programmed to perform certain predetermined modes of operation as desired.

In yet another aspect, a method of operating an interventional catheter having an elongated, flexible catheter shaft and an actuator is provided. The catheter includes one or more interventional elements on its distal end, preferably a balloon, a stent, or both. If a stent is provided, it preferably includes a plurality of stent segments. The catheter also preferably includes an inner shaft, an outer sheath, and one or more optional intermediate shafts, each of which is operably connected to the actuator. The method comprises advancing the distal end of the shaft to a treatment location within a patient, such as a lesion located within a vessel in the patient's vasculature. A selector located on the actuator is placed at a first setting, corresponding with a paving mode of operation, and a knob is rotated around a longitudinal axis of the actuator, thereby causing retraction of the outer sheath relative to the inner shaft. The interventional element is then deployed. The selector is then placed at a second setting, corresponding with a resetting mode of operation, and the actuator knob is rotated around the longitudinal axis of the actuator to cause the outer sheath to advance relative to the inner shaft.

In some embodiments, the selector is placed at a setting corresponding with a separating mode of action and the actuator knob is rotated to create a separation between stent segments that are being deployed, and those that are retained within the catheter outer sheath. The selector setting corresponding with the separating mode of action may be the same as the selector setting corresponding with the resetting mode of action. In such a case, the actuator knob is rotated a first direction to perform the separating process, and is rotated in the opposite direction to perform the resetting process.

In some embodiments, the actuator knob is rotated in the same direction to perform all of the paving, separating, and resetting processes. In these embodiments, the selector member is preferably placed in a different position for each of the three processes.

Other systems, methods, features and advantages of the invention will be or will become apparent to those skilled in the art upon examination of the following figures and detailed description of the preferred embodiments. It is intended that all such additional systems, methods, features, and advantages be included within this description, be within the scope of the invention, and be protected by the accompanying claims. It is also intended that the invention not be limited to the details of the example embodiments.

BRIEF DESCRIPTION OF THE DRAWINGS

FIG. 2A shows an inset view of a portion of the exploded view shown in FIG. 2.

FIG. 3A shows an inset view of a portion of the handle member shown in FIG. 3.

FIGS. 11A-E are side cut-away views of a stent delivery catheter of the invention positioned in a vessel, illustrating various steps of delivering a prosthesis according to the method of the invention.

DETAILED DESCRIPTION OF THE PREFERRED EMBODIMENTS

Figure 1:
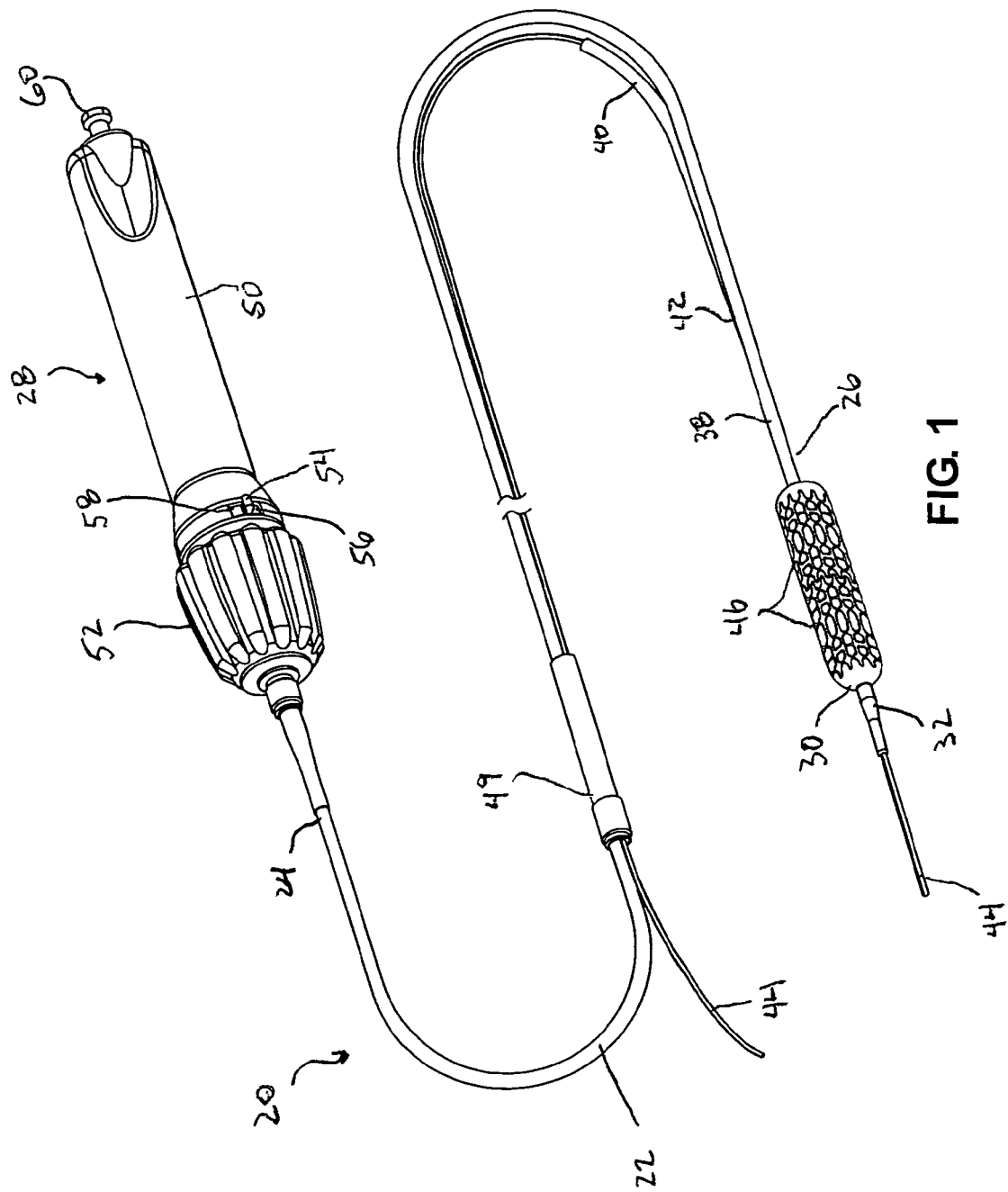
FIG. 1 is a perspective view of a stent delivery catheter according to the invention with the sheath retracted and expandable member inflated.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which these inventions belong. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

The present invention provides devices and methods for operating and controlling interventional apparatus such as catheters with greater control, precision, and visibility. In one aspect, the devices and methods of the invention facilitate operating and controlling an interventional element on a catheter. In an exemplary embodiment, the interventional element is an expandable member such as a balloon for dilatation of vascular lesions. The interventional element also may comprise a stent or series of stent segments. However, the principles of the invention will have applicability to various types of interventional elements for use in various parts of the body, wherever highly precise catheter manipulation and control may be desirable.

Turning to FIGS. 1 and 11A-E, in a first embodiment of the invention, a stent delivery catheter 20 comprises an elongated flexible shaft 22 having a proximal end 24 and a distal end 26. The shaft 22 is comprised of a plurality of coaxial members including an inflation shaft 34, a pusher 36, and a sheath 38. A handle 28 is attached to the sheath 38 at its proximal end 24.

Near the distal end 26, an expandable member 30, shown in an expanded configuration, is mounted at its proximal end to the inflation shaft 34. A guidewire tube 40 extends through a port 42 in the sheath 38 and extends through the interior of the expandable member 30 to the distal end 26 of the shaft. The expandable member 30 is attached at its distal end to the guidewire tube 40, and a nosecone 32 is attached to the guidewire tube 40 distally of the expandable member 30. A guidewire 44 is slidably positionable through the guidewire tube 40 and the nosecone 32 to facilitate guidance of the catheter 20 through the vasculature. A slider assembly 48 is slidably positioned over the catheter shaft 22 and the guidewire 44 at a position between the proximal and distal ends of the catheter shaft 22. The slider assembly 48 includes a relatively rigid member insertable through a sealing valve, such as a hemostasis valve, and sealed therein while providing the ability for the sheath 38 and the guidewire 44 to slide through the slider assembly.

A plurality of stent segments 46 are slidably positioned over the expandable member 30. Additional stent segments 46 are carried within the catheter over the inflation shaft 34 and within the sheath 38. The pusher 36 is axially slidable relative to the inflation shaft 34 and engages the stent segments 46 at its distal end. With the expandable member 30 in its contracted state, the pusher 36 may be advanced distally to advance the stent segments 46 over the expandable member 30, or the pusher 36 may be held in a stationary position while the expandable member 30 is drawn proximally relative to the stent segments 46. The sheath 38 is axially movable relative to the expandable member 30, the pusher 36, and the stent segments 46. The sheath may be repositioned proximally or distally to selectively expose a desired length of the expandable member 30 and the stent segments 46 thereon according to the length of the lesion to be treated. The sheath 38 and the pusher 36 may be drawn proximally in tandem relative to the expandable member 30 to separate the stent segments 46 exposed distally of the sheath 38 from the stent segments 46 held within the sheath 38. Various other aspects of the construction of the delivery catheter 20 and the stent segments 46 are described in copending U.S. patent application Ser. No. 10/637,713, entitled "Apparatus and Methods for Deployment of Vascular Prostheses," filed Aug. 8, 2003, and U.S. Patent Application Ser. No. 60/688,896, entitled "Apparatus and Methods for Deployment of Multiple Custom-Length Prostheses (I)," filed Jun. 8, 2005, each of which applications is incorporated herein by reference.

A stent valve 48 is attached to the interior of the sheath 38 and is preferably spaced proximally from the distal end of the sheath 38 a distance equal to the length of about ½ to 1 stent segment. The stent valve 48 comprises an annular ridge or ring configured to frictionally engage the stent segments 46 to facilitate control of the spacing between those segments to be deployed distally of the sheath 38 and those to be retained within the sheath 38. The stent valve 48 may comprise any of the structures described in the United States patent applications listed in the preceding paragraph, or those described in copending U.S. patent application Ser. No. 10/412,714, filed Apr. 10, 2003 (hereinafter "the '714 application"), which is incorporated herein by reference. For example, as described in the '714 application, the stent valve 48 can be constructed to provide active operation by including a stent valve actuator on the handle 28 that is operatively coupled to the stent valve 48 and that causes the stent valve 48 to selectively engage and disengage the stent segments. The stent valve actuator may comprise, for example, an inflation device, an electronic switch, a mechanical actuator, or the like. The stent valve actuator is preferably positioned on the handle and operated in a manner that allows one-handed operation of the stent valve actuator and the other handle components.

The handle 28 includes a housing 50 and an actuator knob 52 rotatably coupled thereto. A lever 54 attached to a selector 56 extends through a slot 58 formed in the housing near its distal end. As explained in greater detail below, rotation of the actuator knob 52 will cause either or both of the sheath 38 and/or the pusher 36 to advance or retract relative to the inflation shaft 34 and expandable member 30, depending upon the position of the selector 56 and the direction in which the actuator knob 52 is rotated. In a first position of the selector 56, which corresponds to a paving operation, rotation of the actuator knob 52 in a first direction (e.g., counterclockwise) will cause the sheath 38 to retract while the pusher 36 is held in place relative to the sheath 38, thereby exposing one or more stent segments 46 aligned on the expandable member 30. In a second position of the selector 56, which corresponds to both a separation operation and a resetting operation, rotation of the actuator knob 52 in the first direction will cause both the sheath 38 and the pusher 36 to retract relative to the expandable member 30, thereby separating the stent segments 46 retained within the sheath 38 (which are engaged by the stent valve) from those deployed distally of the sheath 38 during the paving operation. While the selector 56 remains in the second position, rotation of the actuator knob 52 in the second direction, opposite of the first direction, will cause both the sheath 38 and the pusher 36 to advance relative to the expandable member in order to reset the device. When the sheath 38 has advanced to its distal-most position, the selector 56 may be placed back to the first position and the process repeated.

A luer fitting 60 extends from the proximal end of the housing 50. The luer fitting 60 is in fluid communication with an inflation lumen in the inflation shaft 34. The luer fitting 60 is adapted for coupling to an inflation device to enable delivery of an inflation fluid into the expandable member 30. An example of a suitable inflation device is the Indeflatorm™ inflation device available from Guidant Corporation of Santa Clara, Calif.

Figure 2:
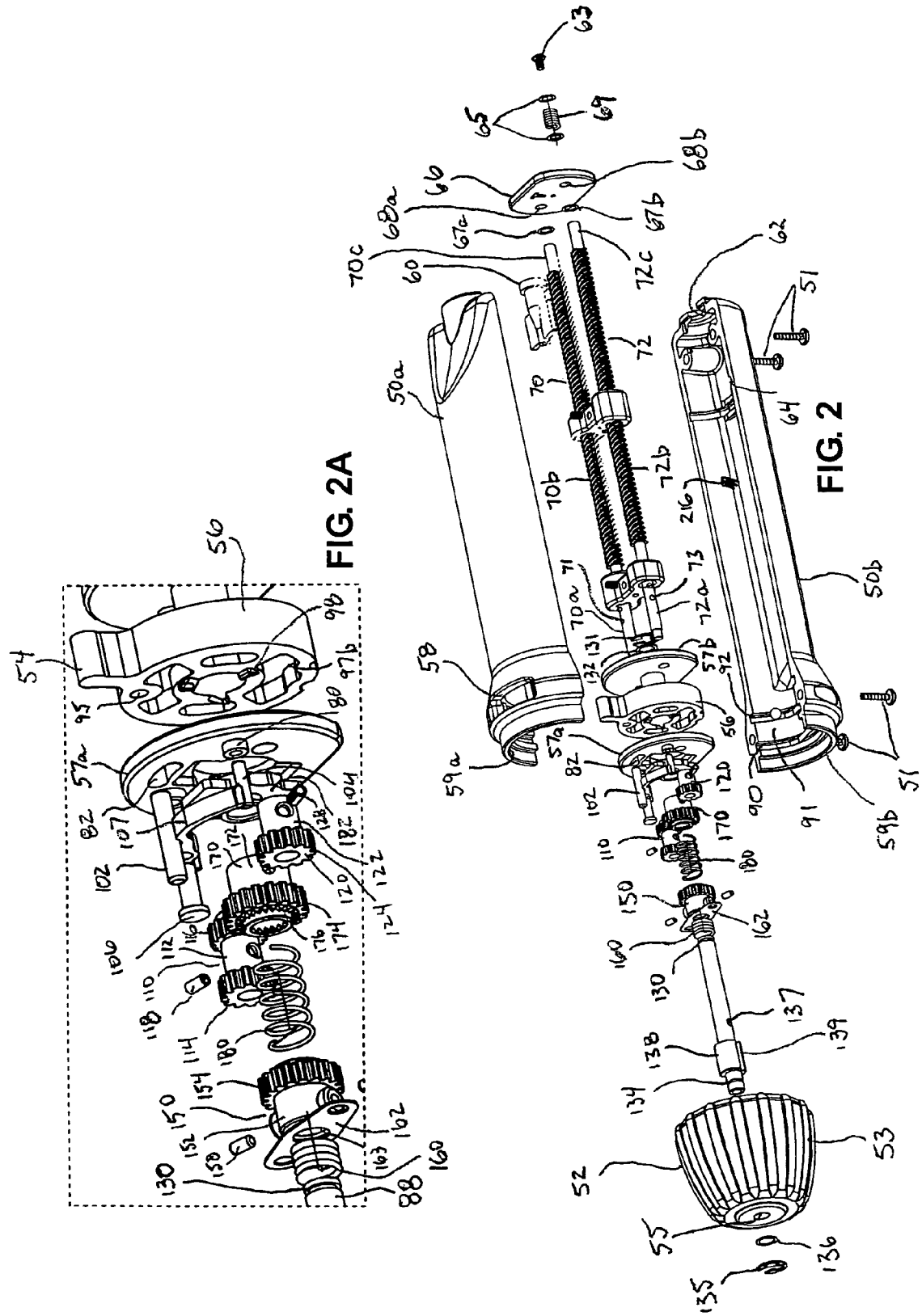
FIG. 2 shows an exploded view of a handle member of the stent delivery catheter shown in FIG. 1.
Figure 3:
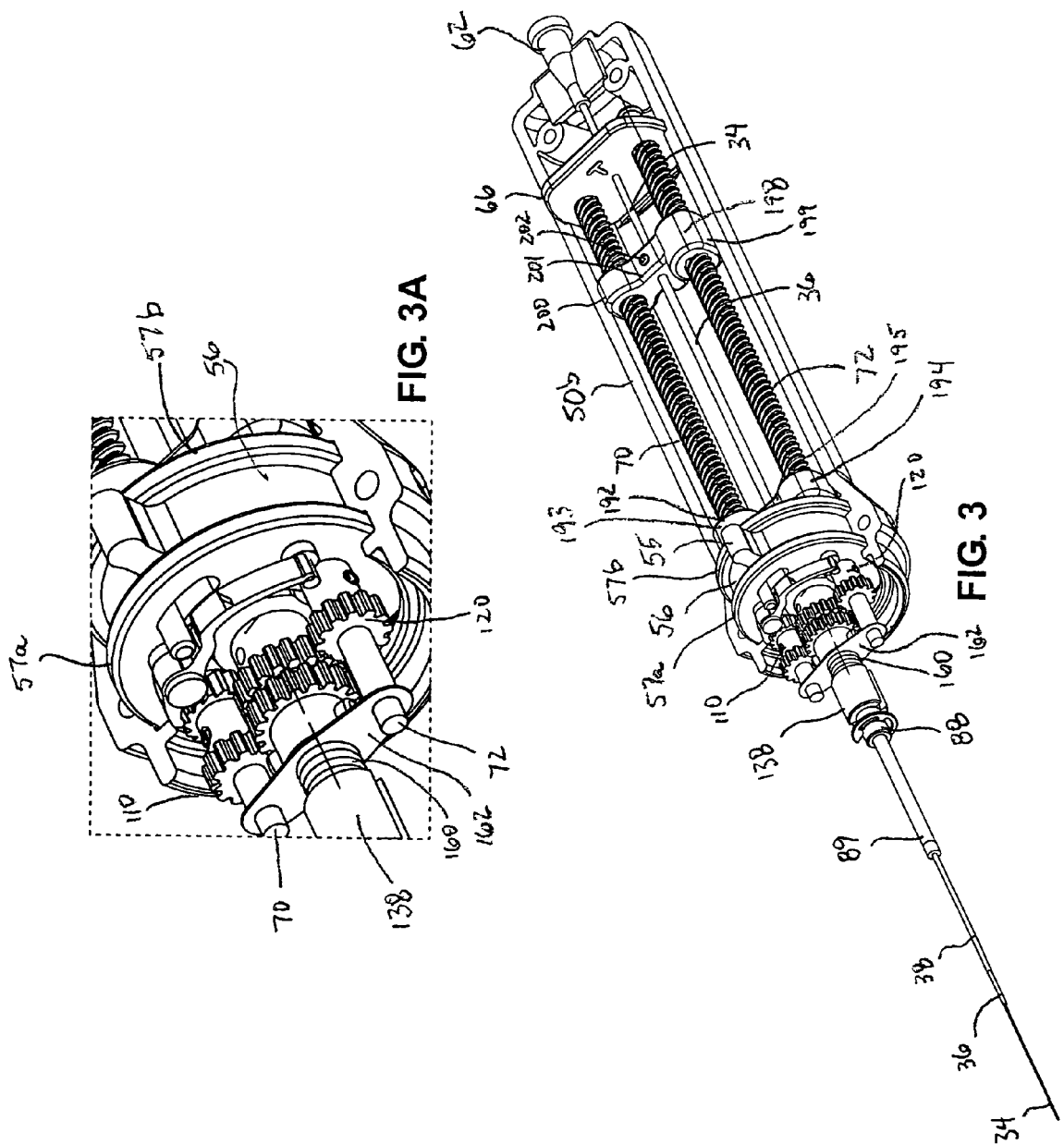
FIG. 3 shows a perspective view of a handle member of the stent delivery catheter with the upper housing and adjustment knob removed.
Figure 4:
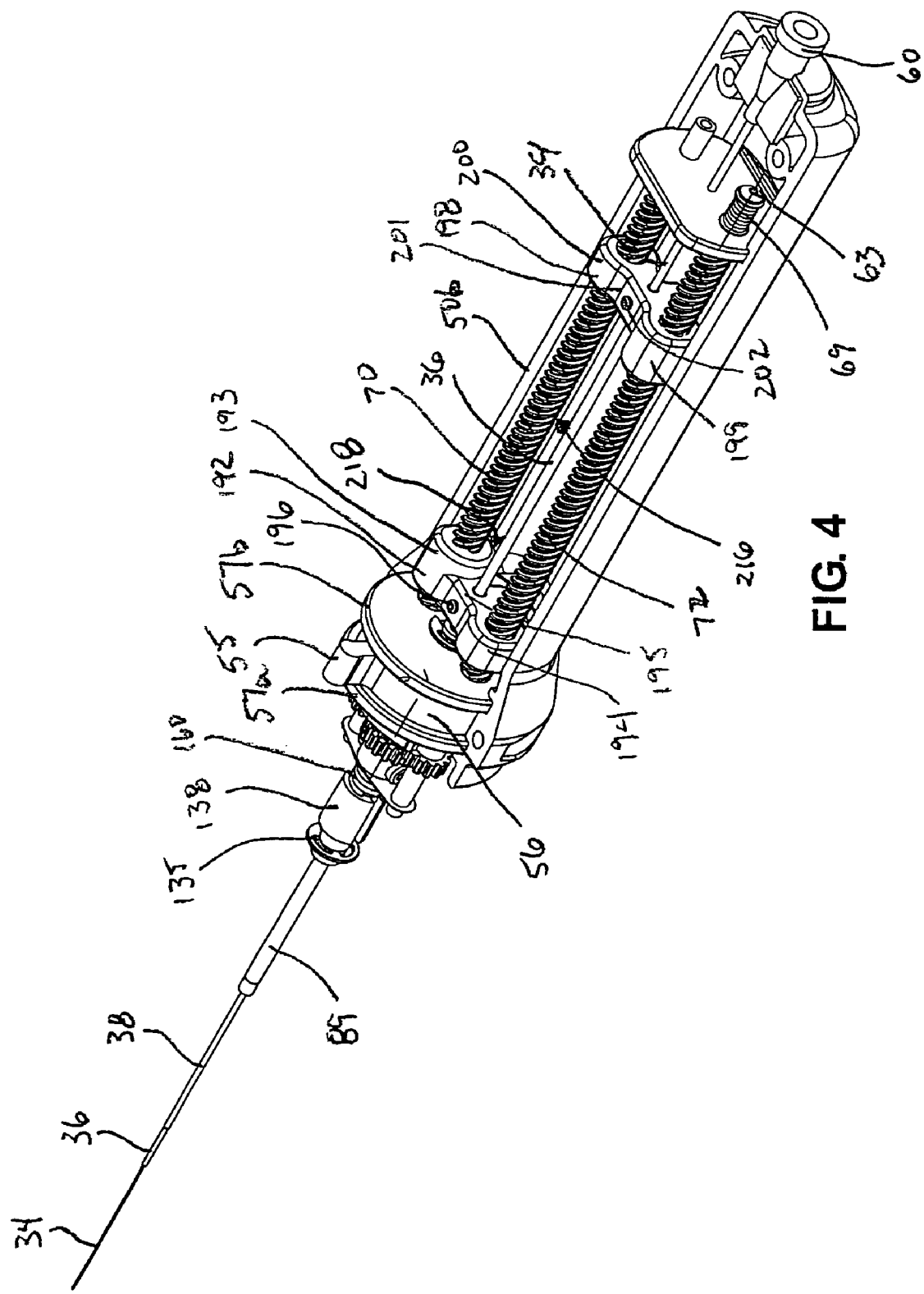
FIG. 4 shows another perspective view of the handle member shown in FIG. 3.

Turning to FIGS. 2 and 2A, the internal structure of the handle 28 is illustrated. The housing 50 includes an upper housing member 50a and a lower housing member 50b. The upper housing member 50a and lower housing member 50b are joined together by four screws 51 that pass through holes formed in the lower housing member 50b and screw into holes formed on the lower facing upper housing member 50a. At their proximal ends, each of the upper housing member 50a and lower housing member 50b includes a recess 62a, 62b adapted to receive and retain the luer fitting 60. Each of the upper housing member 50a and lower housing member 50b also includes a bulkhead slot 64 formed on their respective interior surfaces nearer to the proximal end than the distal end of the housing 50. The bulkhead slot 64 is adapted to receive and retain a proximal bulkhead 66, and to fix the position of the proximal bulkhead 66 within the housing 50 when the housing is assembled. The proximal bulkhead 66 is a flat member having generally rounded side edges and flat upper and lower edges, and includes a pair of laterally spaced through-holes 68a, 68b which are adapted to receive and rotatably retain a first lead screw 70 and a second lead screw 72, as explained more fully below.

The distal ends of the upper housing member 50a and lower housing member 50b each include a radially enlarged section 59a, 59b, respectively. Together, the radially enlarged sections 59a-b enclose and retain the selector 56, a distal selector guide 57a, and a proximal selector guide 57b. The distal selector guide 57a is a generally disc-shaped member having a flat bottom edge. The distal selector guide 57a includes a first pair of through-holes 74a, 74b which are adapted to receive and rotatably retain the first lead screw 70 and second lead screw 72. The distal selector guide 57a also includes a round center aperture 76 adapted to receive a drive shaft 88 therethrough, and to provide a communication space to the selector 56 located just proximally of the distal selector guide 57a. Finally, the distal selector guide 57a is also provided with an upper recess 78a and lower recess 78b on its distal-facing surface, a first pin-guide 80 and a second pin guide 81 also on its distal-facing surface, and a lock-out pin slot 82 near its upper edge. The distal selector guide 57a has a shape and size configured to fit securely in a distal selector guide slot 90 provided on the interior surface of the assembled housing 50.

The proximal selector guide 57b is also a generally disc-shaped member having a flat bottom edge. The proximal selector guide 57b includes a pair of through-holes 84a, 84b which are adapted to receive and rotatably retain the first lead screw 70 and second lead screw 72. The proximal selector guide also includes a round center aperture 86 adapted to receive and rotatably retain the drive shaft. The proximal selector guide 57b has a shape and size configured to fit securely in a proximal selector guide slot 92 provided on the interior surface of the assembled housing 50.

Figure 10:
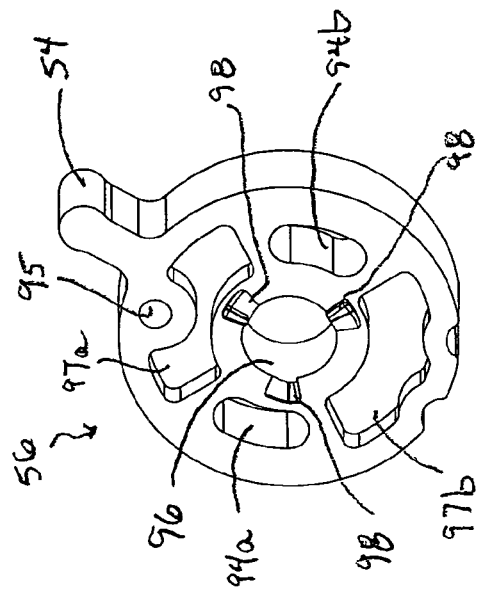
FIG. 10 shows a perspective view of a selector switch.

The selector 56 is a generally disc-shaped member having the selector lever 54 extending radially from its upper edge. (See also FIG. 10). The selector 56 includes a first pair of elongated slots 94a, 94b which are adapted to allow passage of the first lead screw 70 and second lead screw 72 through the selector 56, even as the selector is rotated about a central axis. The selector 56 also includes a round center aperture 96 adapted to receive and rotatably retain the drive shaft 88, and an elongated upper slot 97a and lower slot 97b provided on either side of the center aperture 96. The selector also includes a pin-hole 95 that is adapted to receive and retain a lock-out pin 102, which extends through the lock-out pin slot 82 on the distal selector guide 57a. Finally, the selector 56 is also provided with three ramps 98 on its distal-facing surface, the ramps 98 being spaced equidistantly around the center aperture 96. Each of the ramps 98 is an inclined surface extending distally from the distal face of the selector 56. The selector 56 has a shape and size configured to fit securely in a selector slot 91 provided on the interior surface of the assembled housing 50, and to be sandwiched between the distal selector guide 57a and the proximal selector guide 57b. As noted previously, the selector lever 54 extends through the slot 58 provided on the upper housing member 50a to provide the user access to rotate the selector 56 through a limited range of motion.

The first lead screw 70 and second lead screw 72 are elongated shafts having distal portions 70a, 72a that are not threaded, center portions 70b, 72b that are threaded, and proximal portions 70c, 72c that are not threaded. The distal portions 70a, 72a of the lead screws extend through the through-holes 74a-b, 84a-b provided on the distal selector guide 57a and proximal selector guide 57b, respectively, and through the slots 94a-b provided on the selector 56, and extend a distance distally from the distal surface of the distal selector guide 57a. (See, e.g., FIGS. 3, 3A, 5, and 6). The proximal portions 70c, 72c of each of the lead screws extend through a washer 67a, 67b and through the through-hole 68a, 68b provided on the proximal bulkhead 66. A retaining screw 63 attaches the second lead screw to the bulkhead 66 through a retaining washer 65 and a retaining spring 69. The retaining screw 63, retaining washer 65, and retaining spring 69 attaches the second lead screw 72 to the bulkhead 66 in a manner that prevents the second lead screw 72 from unintended rotation due to forces imparted to the pusher tube 36 by the outer sheath 38 during retraction of the outer sheath 38.

At the distal end of the handle 28, a first lead screw gear 110 is positioned to be received over the distal end of the first lead screw 70. The first lead screw gear includes a cylindrical collar portion 112 that is slidably received on the lead screw 70. A primary set of teeth 114 are provided on the distal end of the first lead screw gear 110, and a secondary set of teeth 116 are provided on the proximal end of the first lead screw gear 110. A gear pin 118 extends through a pin-hole 119 on the collar 112, and also extends through a pin-hole 71 located near the distal end of the first lead screw 70, thereby retaining the first lead screw gear 110 on the distal end of the first lead screw 70.

Similarly, a second lead screw gear 120 is positioned to be received over the distal end of the second lead screw 72. The second lead screw gear includes a cylindrical collar portion 122 that is slidably received on the second lead screw 72. A primary set of teeth 124 are provided on the distal end of the second lead screw gear 120. A gear pin 128 extends through a pin-hole 129 on the collar 122, and also extends through a pin-hole 73 located near the distal end of the second lead screw 72, thereby retaining the second lead screw gear 120 on the distal end of the second lead screw 72.

The drive shaft 88 is an elongated, cylindrical member that extends through the center apertures 76, 96, 86 of the distal selector guide 57a, selector 56, and proximal selector guide 57b. The drive shaft 88 is hollow, providing an interior passage through which the sheath 38, pusher 36, and inflation shaft 34 are able to pass, as described more fully below. The proximal end of the drive shaft 88 includes a peripheral slot 130 that is adapted to receive a retaining clip 131 that retains the proximal end of the drive shaft 88 against the proximal side of the proximal selector guide 57b. A disc washer 132 is placed between the retaining clip 131 and the proximal selector guide 57b to facilitate rotation of the drive shaft 88. Similarly, the distal end of the drive shaft 88 includes a peripheral slot 134 that is adapted to receive another retaining clip 135 that retains the distal end of the drive shaft 88 against the distal end of the actuator knob 52. A disc washer 136 is placed between the retaining clip 135 and the actuator knob 52. A slotted collar 138 is attached to the drive shaft 88 proximally of its distal end. The slotted collar 138 is a cylindrical member having a diameter that is slightly larger than that of the drive shaft 88. The slotted collar 138 includes a pair of longitudinal slots 139 on opposed sides thereof. A slotted pin-hole 137 is formed through the drive shaft to provide a mechanism for connecting a primary drive gear 150 to the shaft 88, as described below.

Figure 5:
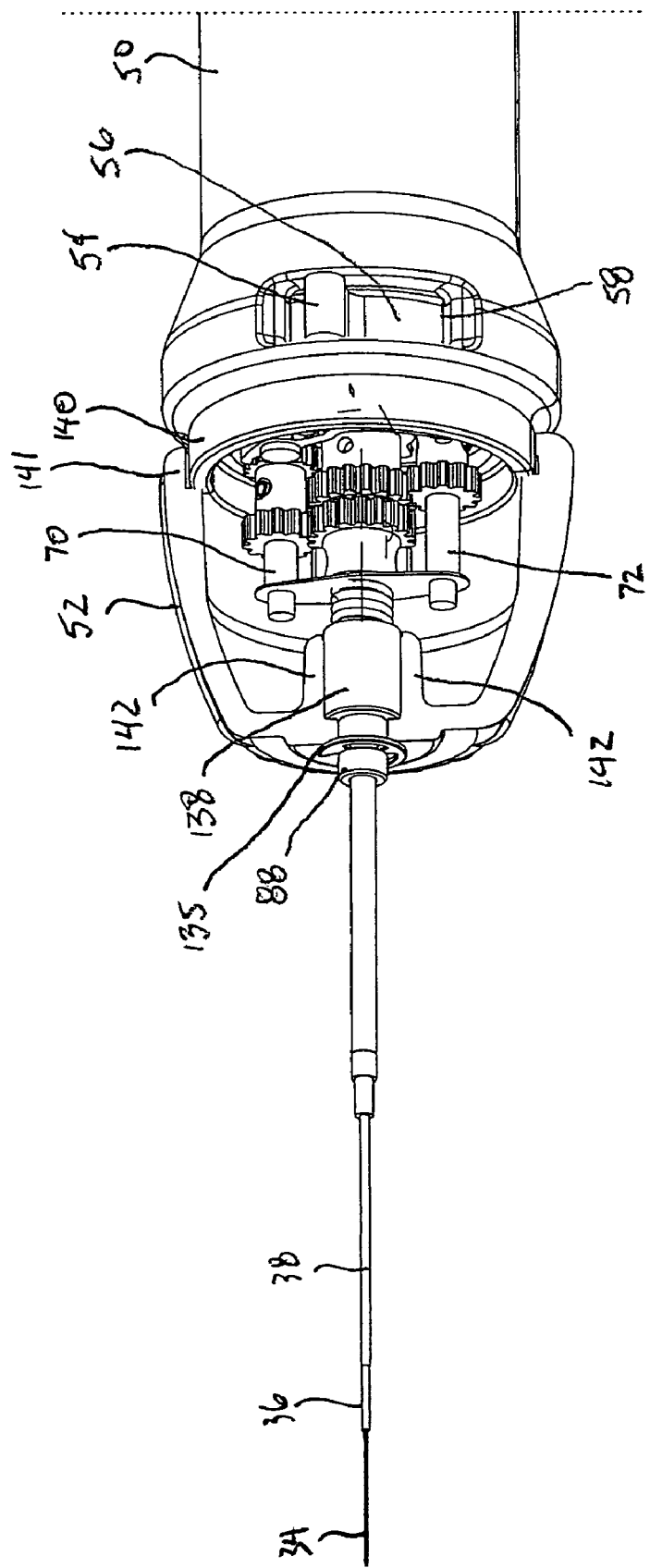
FIG. 5 shows a partial cross-sectional view of the distal portion of the handle member.
Figure 6:
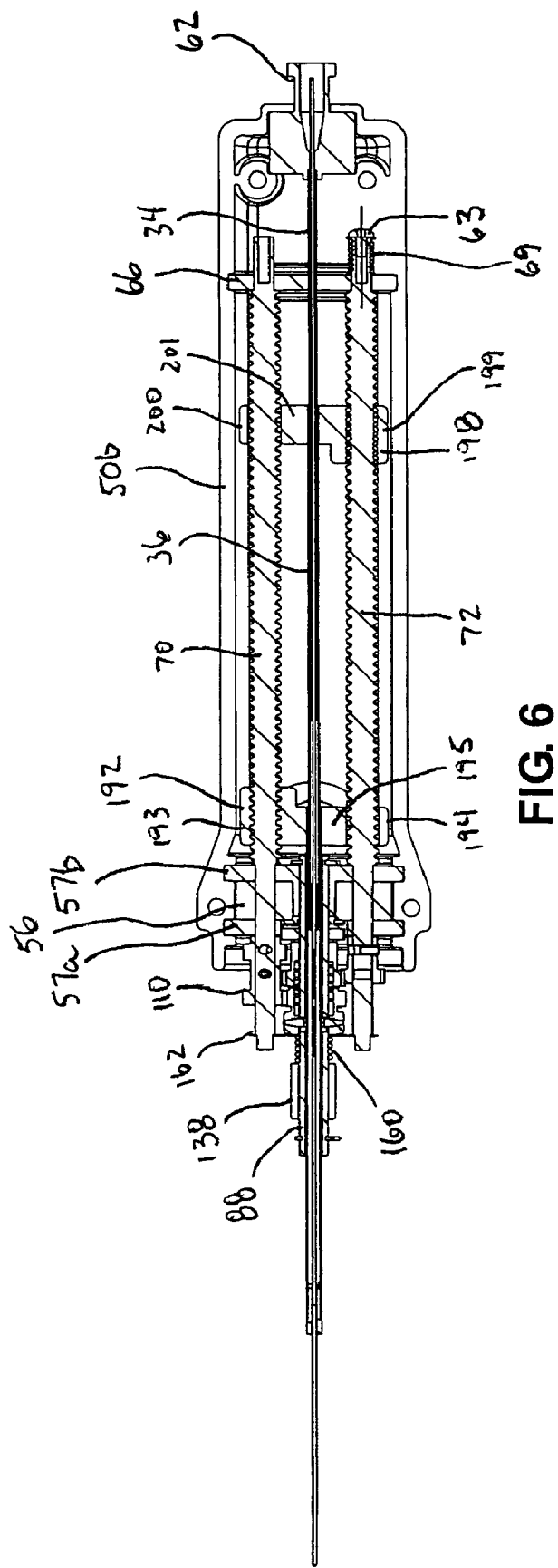
FIG. 6 shows a full cross-sectional view of the handle member with the adjustment knob removed.

The actuator knob 52 is a generally cup-shaped member having a plurality of knurls 53 formed on its outer surface. The distal end of the actuator knob 52 includes a through-hole 55 that allows passage of the drive shaft 88 therethrough, as described above. Referring to FIG. 5, the open proximal end of the actuator knob 52 includes a circumferential lip 141 that rotatably rests against the distal edge 140 of the housing 50. In addition, the interior surface of the actuator knob 52 has a pair of tabs 142 extending proximally from the interior distal surface of the knob. The tabs 142 are of a size and configuration to slidably engage the slots 139 on the slotted collar 138 that is attached to the distal end of the drive shaft 88. Thus, when the tabs 142 on the actuator knob 52 are engaged with the slots 139 on the slotted collar 138, rotation of the actuator knob 52 causes the drive shaft 88 to rotate.

Figure 8:
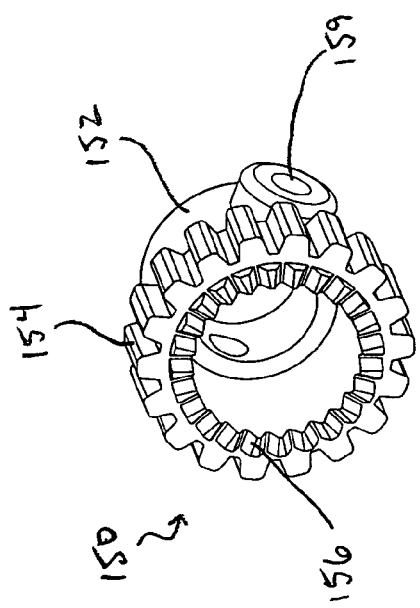
FIG. 8 shows a perspective view of an integrated gear and collar.

As noted above, the primary drive gear 150 is positioned to be received over the drive shaft 88. The primary drive gear 150 includes a cylindrical collar portion 152 that is slidably received on the drive shaft 88. (See also FIG. 8). A primary set of teeth 154 are provided on the proximal end of the primary drive gear 150 facing radially outward. A secondary set of teeth 156 are provided on the proximal end of the primary drive gear 150 facing proximally, i.e., toward the proximal end of the handle 28. A pair of gear pins 158 extend through a pin-hole 159 on the collar 152, and also extends through the pin-hole 137 on the drive shaft 88, thereby retaining the primary drive gear 150 on the drive shaft 88.

A distal spring 160 is located over the drive shaft 88 and its distal end rests against the proximal edge of the slotted collar 138 on the drive shaft 88. The proximal end of the distal spring 160 rests against a lead screw support member 162. The lead screw support member 162 is a flat, generally oval-shaped member having a center aperture 163 and a through-hole 164a, 164b on either side of the center aperture 163. The drive shaft 88 extends through the center aperture 163 of the lead screw support member 162. The distal side of the lead screw support member 162 rests against the primary drive gear 150, which is fixed to the drive shaft 88. The distal end of the first lead screw 70 passes through one of the through-holes 164a of the lead screw support member 162, while the distal end of the second lead screw 72 passes through the other of the through-holes 164b of the lead screw support member 162.

A secondary drive gear 170 is positioned to be received over the drive shaft 88. The secondary drive gear 170 includes a cylindrical collar portion 172 that is slidably received on the drive shaft 88. A primary set of teeth 174 are provided on the distal end of the secondary drive gear 170 facing radially outward. A secondary set of teeth 176 are provided on the distal end of the secondary drive gear 170 facing distally, i.e., toward the primary drive gear 150. The secondary drive gear 170 is not pinned to the drive shaft 88. Instead, the secondary drive gear 170 is able to move axially along the drive shaft 88, as explained below. A drive gear spring 180 is located over the drive shaft 88 and between the primary drive gear 150 and the secondary drive gear 170. Thus, the drive gear spring 180 provides a force biasing the secondary drive gear 170 proximally, away from the primary drive gear 150 (which is fixed relative to the drive shaft 88).

Figure 9:
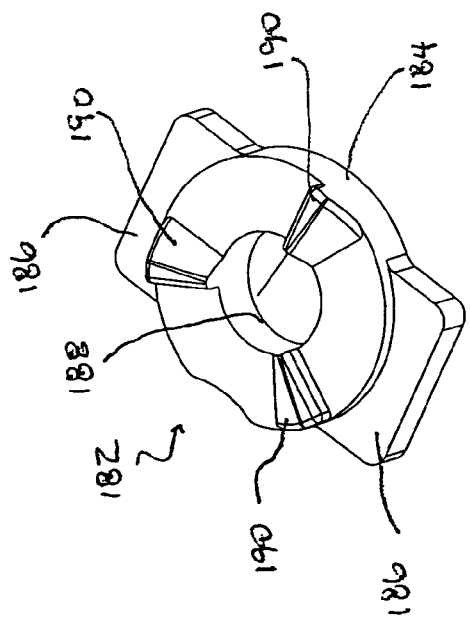
FIG. 9 shows a perspective view of a gear advancer.

A gear advancer 182 is located just proximal of the secondary drive gear 170. The gear advancer is illustrated in FIG. 9, and includes a disc-shaped central portion 184 and a pair of tabs 186 located on opposed sides of the central portion 184. The gear advancer 182 further includes a center aperture 188 adapted to slidably receive the drive shaft 88, and three identical ramps 190 spaced equidistantly around the center aperture 188. Each of the ramps 190 is an inclined surface extending from the proximal face of the gear advancer 182. Turning back to FIGS. 2, 2A, 3, and 3A, the gear advancer 182 is located on the drive shaft 88 between the secondary drive gear 170 and the distal selector guide 57a. The gear advancer tabs 186 each have a size and shape configured to positively engage the upper and lower recesses 78a, 78b of the distal selector guide 57a.

The ramps 190 on the proximal face of the gear advancer 182 are directed toward and are in contact with the distal face of the selector 56 through the center aperture 76 of the distal selector guide 57a. When the selector 56 is rotated, the ramps 98 of the selector 56 engage the ramps 190 on the gear advancer 182, causing the gear advancer 190 to separate from the selector 56, which is fixed axially within the housing 50. The separation force against the gear advancer 182 causes the gear advancer and the secondary drive gear 170 to move distally along the drive shaft 88 against the spring force of the drive gear spring 180. When the selector 56 is rotated fully, i.e., when the peaks of the selector ramps 98 are engaged with the peaks of the gear advancer ramps 190, the secondary teeth 176 of the secondary drive gear 170 come into engagement with the secondary teeth 156 of the primary drive gear 150, thereby causing the secondary drive gear 170 to rotate in unison with the primary drive gear 150. When the secondary teeth 176 of the secondary drive gear are not in contact with the secondary teeth 156 of the primary drive gear 150, the secondary drive gear 170 does not rotate but instead floats on the drive shaft 88.

As noted above, a lock-out pin 102 extends through a lock-out pin slot 82 on the distal selector guide 57a and into a pin-hole 95 on the selector 56. A first fixed pin 104 extends distally from the first pin guide 80 on the distal selector guide 57a, and a second fixed pin 106 extends distally from the second pin guide 81 on the distal selector guide 57a. A rocker arm 107 is pivotably attached to the second fixed pin 106. A first end 108 of the rocker arm rests against the first fixed pin 104. The opposite end 109 of the rocker arm is a pawl that selectively engages the secondary teeth 116 of the first lead screw gear 110. Together, the lock-out pin 102, the rocker arm 107, and the secondary teeth 116 of the first lead screw gear 110 function as a lock-out device that prevents rotation of the first lead screw 70 during some operations, as described more fully below.

Referring to FIGS. 3-6, a paving nut 192 is located within the housing 50 and includes a first cylindrical section 193 that is located on the first lead screw 70, and a second cylindrical section 194 that is located on the second lead screw 72. A bridge section 195 extends between and interconnects the first cylindrical section 193 and the second cylindrical section 194. A set screw 196 extends through the bridge section 195 and attaches the paving nut 192 to the sheath 38, which extends through the drive shaft 88 and through an outer support shaft 89 on the distal end of the handle 28. The first cylindrical section 193 of the paving nut 192 is threaded internally such that it will ride along the threads of the first lead screw 70 as the first lead screw is rotated. The second cylindrical section 194 is not threaded, and will travel along the second lead screw 72 independently of any rotation of the second lead screw 72. Thus, when the first lead screw 70 rotates, it causes the paving nut 192 to move proximally or distally within the housing 50, depending upon the direction of rotation of the first lead screw 70. As the paving nut 192 moves, it also causes the sheath 38 to advance and retract.

A separation nut 198 is similarly located within the housing 50 and includes a first cylindrical section 199 that is located on the second lead screw 72, and a second cylindrical section 200 that is located on the first lead screw 70. A bridge section 201 extends between and interconnects the first cylindrical section 199 and the second cylindrical section 200. A set screw 201 extends through the bridge section 200 and attaches the separation nut 198 to the pusher 36, which extends coaxially with the sheath 38 through the drive shaft 88 and through the outer support shaft 89 on the distal end of the handle 28. The first cylindrical section 199 of the separation nut 198 is threaded internally such that it will ride along the threads of the second lead screw 72 as the second lead screw is rotated. The second cylindrical section 200 is not threaded, and will travel along the first lead screw 70 independently of any rotation of the first lead screw 70. Thus, when the second lead screw 72 rotates, it causes the separation nut 198 to move proximally or distally within the housing 50, depending upon the direction of rotation of the second lead screw 72. As the separation nut 198 moves, it also causes the pusher 36 to advance and retract.

As noted previously, the inflation shaft 34 extends coaxially through the pusher 36 and the sheath 38, and is attached at its proximal end to the luer fitting 60 on the proximal end of the handle 28. The inflation shaft 34 is therefore fixed in position relative to the handle 28, whereas the sheath 38 subject to advancement and retraction with movement of the paving nut 192, and the pusher 36 is subject to advancement and retraction with movement of the separation nut 198.

Turning now to FIGS. 3-7 and 11A-E, the operation of the first embodiment of the stent delivery catheter 20 will be described. Initially, the sheath 38 is in its fully advanced position, as illustrated, for example, in FIG. 11A. The sheath 38 is adjacent to the nosecone 32, and covers the stent segments 46 that are aligned over the expandable member 30. The pusher 36 is also fully advanced, with its distal end in contact with the proximal-most stent segment 46.

The catheter 20 is advanced over a guidewire 44 through a vessel V until the treatment location is reached, such as a lesion L. The nosecone 32 is advanced distally of the lesion L to place the distal end of the catheter in the proper position for deployment of the stent segments 46.

The sheath 38 is then retracted while the pusher 36 is held in place, in order to expose the distal-most stent segments 46 aligned over the expandable member 30. See FIG. 11B.

Referring to FIGS. 3-7, retraction of the sheath 38 while maintaining the position of the pusher 36 is achieved by causing the paving nut 192 to move proximally within the handle 28 along the first lead screw 70. This movement of the paving nut 192 is caused by, first, placing the selector 56 in the "paving" position by rotating the lever 54 fully clockwise. (NOTE: References herein to "clockwise" and "counter-clockwise" rotation of the selector and actuator knob are from a point of reference at the proximal end of the handle.) In this selector position, the ramps 190 of the gear advancer 182 are not engaged with the ramps 98 of the selector 56, with the result that the gear advancer 182 is in its proximal position. In this position, the gear advancer 182 does not cause the secondary drive gear 170 to engage the primary drive gear 150. Thus, the secondary drive gear 170 rotates freely on the drive shaft 88. Counter-clockwise rotation of the actuator knob 52 causes the drive shaft 88 to rotate (also counter-clockwise), which causes rotation of the primary drive gear 150 (also counter-clockwise), which is engaged with the first lead screw gear 110, thereby causing rotation of the first lead screw 70 (clockwise) and retraction of the paving nut 192. However, rotation of the drive shaft 88 caused by rotation of the actuator knob 52 does not cause rotation of the disengaged secondary drive gear 170, and therefore the second lead screw gear 120 is not rotated. Thus, the paving nut 192 is retracted (thereby causing retraction of the connected sheath 38), while the separation nut 198 is stationary (thereby causing the pusher 36 to remain in place).

Figure 7:
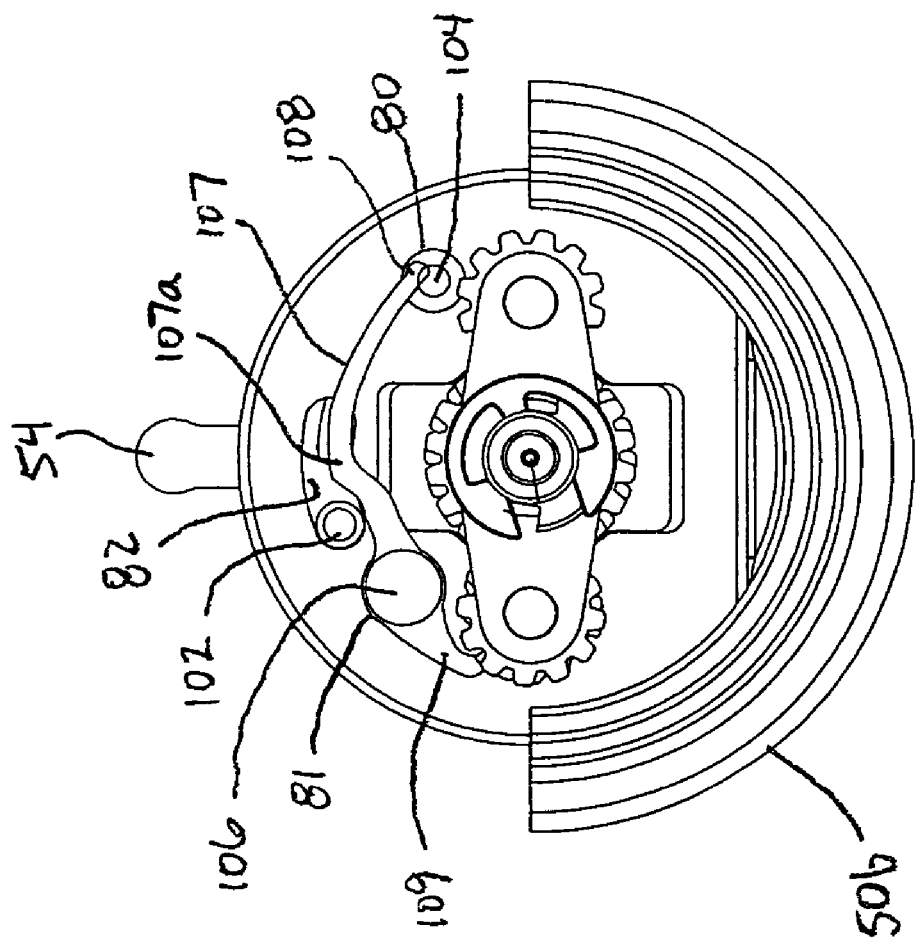
FIG. 7 shows an end view of the handle member with the upper housing and adjustment knob removed.

In addition, the "paving" selector position leaves the lock-out mechanism in the position illustrated in FIG. 7, in which the lock-out pin 102 rests against the rocker arm 107 and the second end 109 of the rocker arm acts as a pawl in engagement with the secondary teeth 116 of the first lead screw gear 110. The ratcheting mechanism between the secondary teeth 116 and the second end 109 of the rocker arm therefore allows the first lead screw gear 110 to rotate clockwise, but prevents counter-clockwise rotation. Stated otherwise, when the selector 56 is in the "paving" position, the lock-out mechanism prevents the first lead screw 70 from rotating counter-clockwise, and, thus, prevents the actuator knob 52, from rotating clockwise. This prevents the user from inadvertently advancing the sheath 38 beyond the initial position or re-sheathing paved stent segments.

After the sheath 38 has been retracted a sufficient distance to expose the desired number of stent segments 46, the separation process is performed. Separation refers to the action of separating the exposed stent segments 46 from the stent segments 46 retained within the sheath 38 in order to allow the expandable member 30 to expand only the exposed stent segments 46 and allow some distance for the balloon taper from the deployed stent segments to the distal end of sheath 38. Separation requires a relatively short distance of retraction of both the sheath 38 and the pusher 36, e.g. 2-4 mm. When both the sheath 38 and the pusher 36 are retracted, the stent valve 48 engages the distal-most stent segment 46 within the sheath 38 and retracts the covered stent segments 46 along with the sheath 38. See FIG. 11C.

Referring to FIGS. 3-7, retraction of the sheath 38 and the pusher 36 simultaneously is achieved by causing the paving nut 192 to move proximally within the handle 28 along the first lead screw 70 while also causing the separation nut 198 to move proximally within the handle 28 along the second lead screw 72. This simultaneous movement of the paving nut 192 and separation nut 198 is caused by, first, placing the selector 56 in the "separation" position by rotating the lever 54 fully counter-clockwise. In this selector position, the ramps 190 of the gear advancer 182 are fully engaged with the ramps 98 of the selector 56, with the result that the gear advancer 182 is advanced to its fully distal position. In this position, the gear advancer 182 causes the secondary drive gear 170 to engage the primary drive gear 150. Thus, the secondary drive gear 170 rotates in unison with the primary drive gear 150. Counter-clockwise rotation of the actuator knob 52 causes the drive shaft 88 to rotate (also counter-clockwise), which causes rotation of the primary drive gear 150 (also counter-clockwise), which is engaged with the first lead screw gear 110, thereby causing (clockwise) rotation of the first lead screw 70 and retraction of the paving nut 192. Simultaneously, (counter-clockwise) rotation of the drive shaft 88 caused by rotation of the actuator knob 52 causes (counter-clockwise) rotation of the engaged secondary drive gear 170, which is engaged with the second lead screw gear 120 and therefore causes (clockwise) rotation of the second lead screw 72. Thus, the paving nut 192 is retracted (thereby causing retraction of the connected sheath 38), as the separation nut 198 is also retracted (thereby causing simultaneous retraction of the pusher 36).

In addition, the "separating" selector position changes the lock-out mechanism from the position illustrated in FIG. 7. Specifically, when the selector 56 is rotated counter-clockwise, the lock-out pin 102 engages the raised upper surface 107a of the rocker arm 107, causing it to deform radially inward (i.e., toward the drive shaft 88). Deformation of the rocker arm upper surface 107a causes the second end 109 of the rocker arm to disengage from the secondary teeth 116 of the first lead screw gear 110. This allows the first lead screw gear 110 to freely rotate either clockwise or counter-clockwise, defeating the lock-out mechanism. Stated otherwise, when the selector 56 is in the "separation" position, the lock-out mechanism is disengaged, allowing the user to rotate the actuator knob 52 in either direction, thereby either advancing or retracting the sheath 38 and pusher 36 to adjust the separation distance.

After the separation process is completed, which entails retracting the sheath 38 and the pusher 36 a distance equal to about the length of ½ to about 1 stent segment 46 or about 2-4 mm, the expandable member 30 is expanded by injecting inflation media through the luer fitting 60 into the lumen of the inflation shaft 34. See FIG. 11D. Expansion of the expandable member causes the exposed stent segments 46 to plastically expand against the lesion L. The expandable member 30 is then contracted by withdrawing the inflation media, leaving the expanded stent segments 46 in place. See FIG. 11E.

As described herein, the catheter 20 is capable of deploying stent segments 46 in multiple locations during a single interventional procedure. Therefore, after deploying the stent segments 46 in the manner described above, the catheter is preferably reset to the initial position, as in FIG. 11A, in order to perform another deployment. Resetting the catheter 20 entails advancing both the sheath 38 and the pusher 36 simultaneously until they reach the initial position. This process is performed by rotating the actuator knob 52 clockwise while the selector 56 remains in the "separation" position (i.e., fully advanced counter-clockwise). Clockwise rotation of the actuator knob 52 causes clockwise rotation of the drive shaft 88, the primary drive gear 150, and the secondary drive gear 170, which, in turn, causes counter-clockwise rotation of the first lead screw gear 110 and the second lead screw gear 120. This causes advancement of the paving nut 192 and the separation nut 198, which advances the sheath 38 and the pusher 36.

Once the sheath 38 and pusher 36 have been advanced fully, the rotation of the actuator knob 52 is stopped, the selector 56 is rotated to the "paving" position, and the catheter 20 is reset and prepared for another deployment.

Figure 12A:
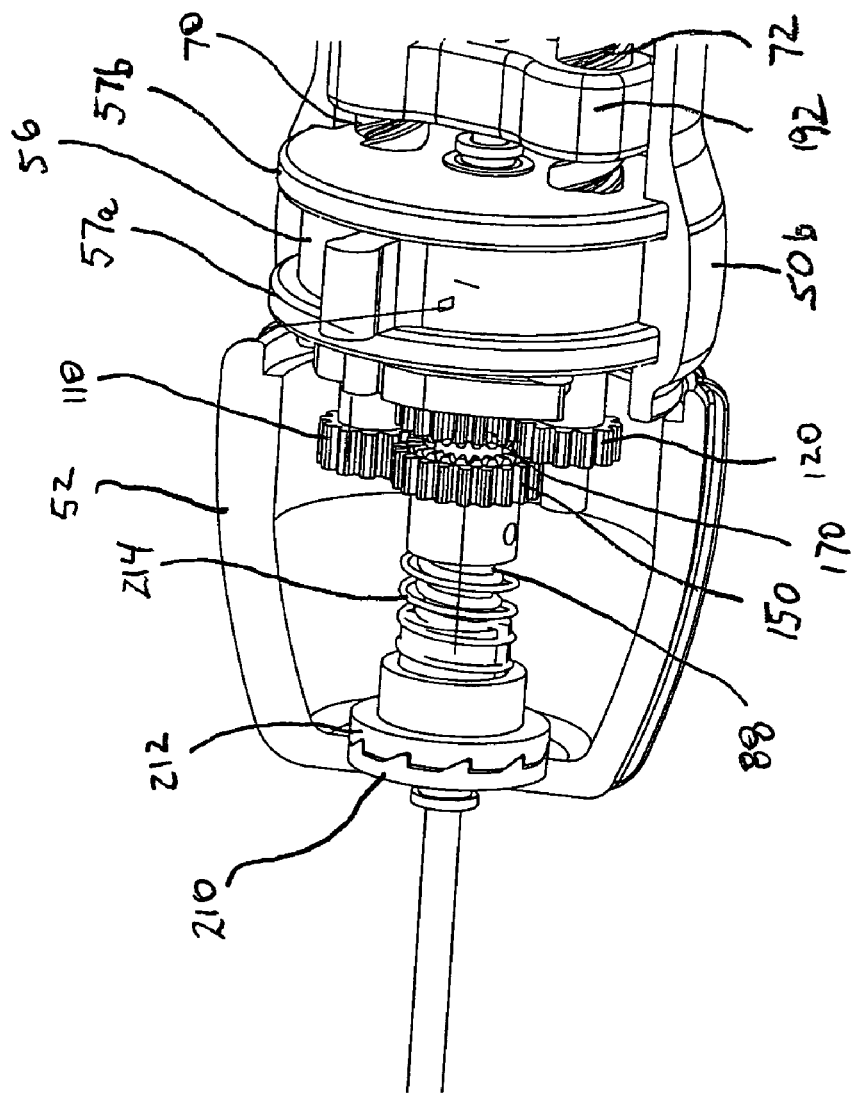
FIGS. 12A and 12B illustrate a reset clutch mechanism.
Figure 12B:
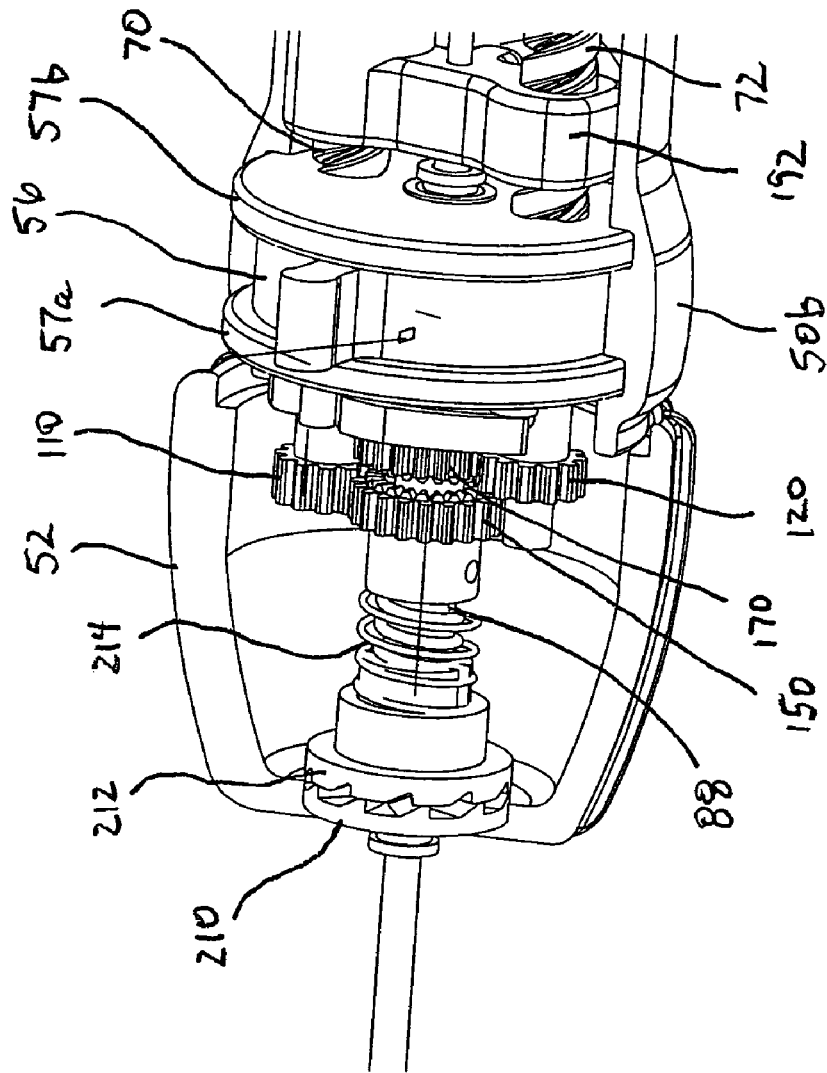

Alternative features may be incorporated in the handle 28 described above. One such feature is the provision of a reset clutch mechanism. The reset clutch mechanism is intended to prevent the user from over-resetting the catheter after stent deployment, i.e., it prevents the user from advancing the sheath 38 and pusher 36 beyond the initial position illustrated in FIG. 11A. Referring to FIGS. 12A-B, a first clutch plate 210 is fixed to the interior surface of the actuator knob 52, with teeth facing proximally. A second clutch plate 212 is fixed to the distal end of the drive shaft 88, which does not extend through a hole in the actuator knob 52. The mating teeth of the second clutch plate 212 face distally, opposed to the first clutch plate 210. The second clutch plate 212 is keyed to the drive shaft 88 such that it is able to slide proximally along the drive shaft 88 but cannot rotate on the shaft. A compression spring 214 is positioned in back of the second clutch plate 212 to bias the second clutch plate distally against the first clutch plate 210. The teeth on the first clutch plate 210 and second clutch plate 212 fully engage during the paving, separation, and resetting processes described above, thereby translating rotation of the actuator knob 52 into rotation of the drive shaft 88. However, if an excessive amount of torque is created due to over-resetting of the catheter, the clutch plates 210, 212 will slip due to displacement of the second clutch plate 212 against the biasing force of the compression spring 214. The amount of torque needed to cause the clutch plates to slip may be adjusted by changing the compression spring 214 or its strength, altering the geometry of the teeth on either or both of the clutch plates 210, 212, changing the materials used to make the clutch plates 210, 212, or other similar mechanisms.

Another alternative feature that may optionally be included in the handle 28 is a paving nut limiting mechanism. The purpose of the paving nut limiting mechanism is to limit the distance that the paving nut 192 is allowed to travel proximally within the housing 50. The limit preferably corresponds to the total length of all of the stent segments 46 carried at the distal end of the catheter 20. Thus, the paving nut limiting mechanism prevents the user from retracting the sheath 38 beyond the point at which stent segments 46 are available for deployment. The paving nut limiting mechanism includes a tab 218 that extends downward from the bottom surface of the paving nut 192, and a mating detent 216 that extends upward from the internal surface of the lower housing member 50*b* at a desired position along the travel path of the paving nut 192. The stationary detent 216 blocks the tab 218, thereby preventing the paving nut 192 from retracting further within the housing 50. Alternatively, the tab may be on the upper surface of the paving nut 192 and the detent on the upper housing member 50*a*. Additionally, the detent 216 may be permanently fixed in position within the housing 50, or its position may be adjustable to allow the operator to select a desired stent length, beyond which the device is prevented from paving.

Still another alternative feature that may optionally be included in the handle 28 is an inflation disabler. The purpose of the inflation disabler is to disable the ability to use the inflation lumen unless the selector 56 is in the "separation" position, thereby preventing the user from inflating the expandable member 30 prior to performing the separation process. There are a number of mechanisms that are suitable for performing the inflation disabling function. For example, an electronically or mechanically switchable valve may be attached to the inflation inlet at the luer fitting 60, with the valve being actuated by the position of the selector 56. The valve may remain closed to prevent introduction of inflation fluid, or the inflation fluid injected through the luer fitting 60 may be diverted by the valve out of the inflation tube 34 unless the selector 56 is in the "separation" position. As another example, a mechanical tubing clamp may be attached to a tube placed between the luer fitting 60 and the inflation shaft 34, whereby the tubing clamp may optionally crimp, flatten, or otherwise close off the tube when the selector 56 is not in the "separation" position. Other inflation prevention mechanisms are also possible.

Still another alternative feature that may optionally be included in the handle 28 is to provide one or more lead screws having sections with threads having variable pitch. For example, a first lead screw may be provided with a section having a first pitch and a section having a second pitch, where the first pitch provides a greater mechanical advantage than does the second pitch. In such a case, the lead screw might provide faster speed, greater feel, or some other desired characteristic over differing operational zones. For example, it may be desirable to perform the paving process at a higher speed than is used during the separation process. Providing a variable pitch lead screw may provide the ability to obtain this result. Alternatively, the primary and secondary drive gears may be replaced with multiple gears having various sizes or pitches to allow the rate of paving and/or separation to be selected by the operator.

Figure 13A:
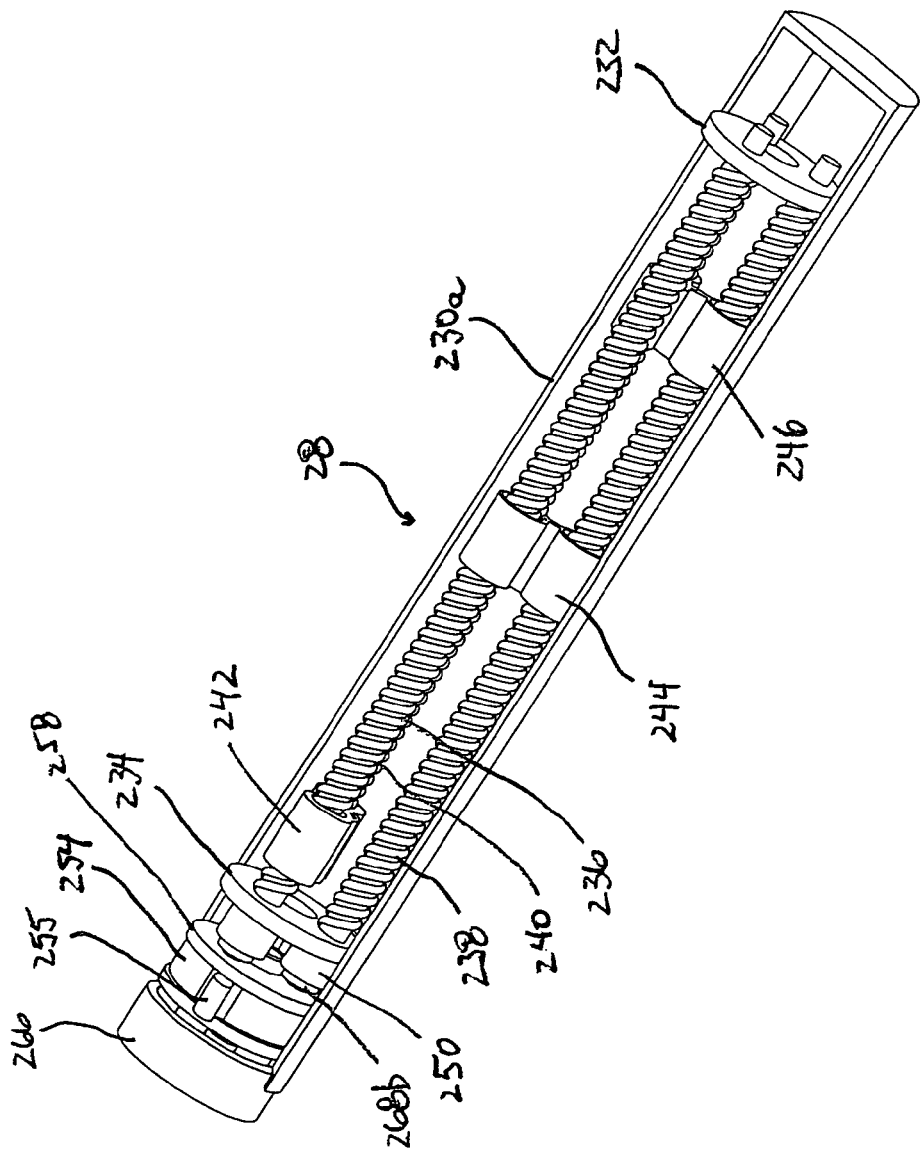
FIG. 13A shows a perspective view of an alternative embodiment of a handle member of the stent delivery catheter with the upper housing removed.
Figure 13B:
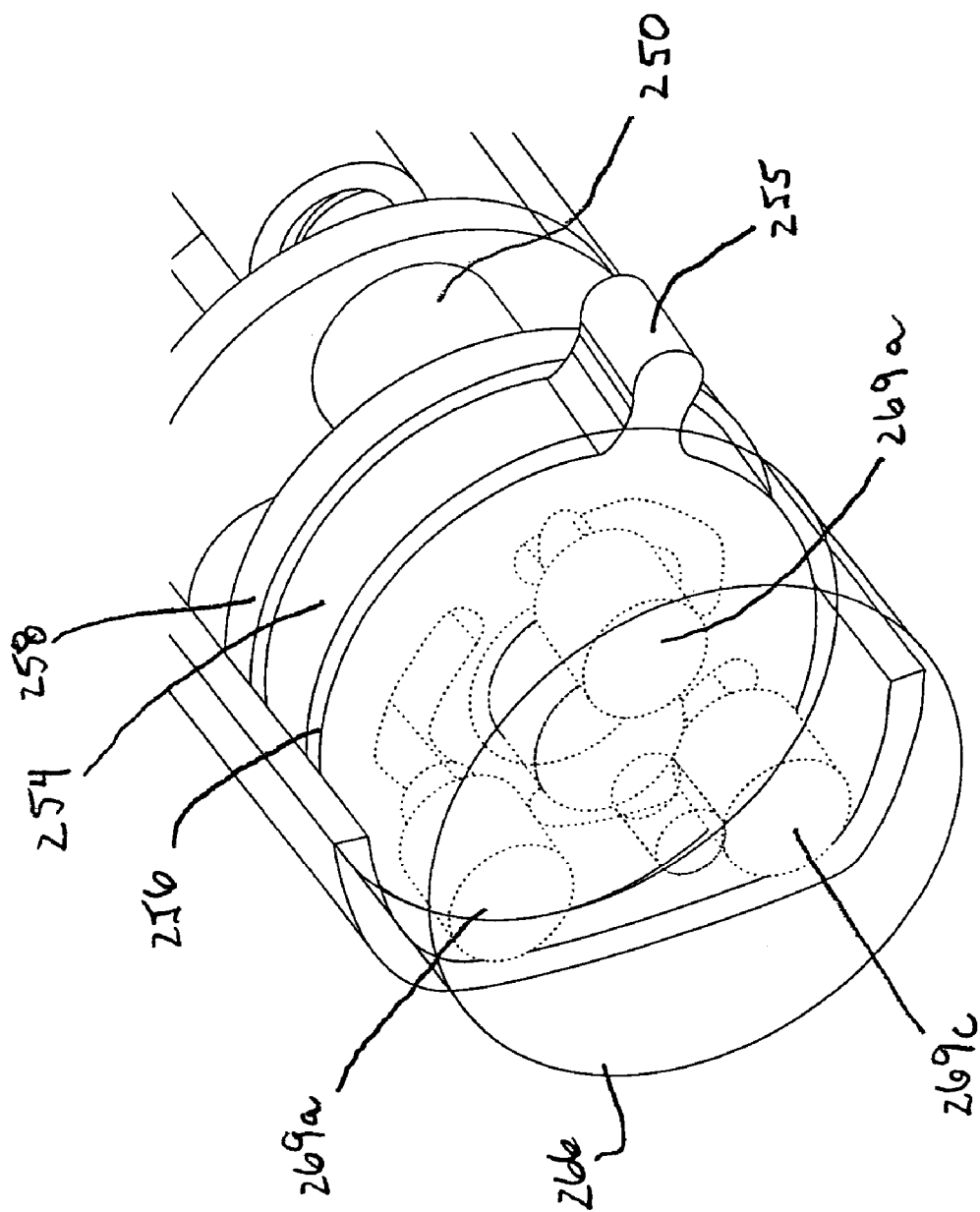
FIG. 13B shows the distal end of the handle member shown in FIG. 13A.

An alternative embodiment of a handle 28 in accordance with the present invention is illustrated in FIGS. 13A and 13B. The alternative embodiment includes three lead screws, thereby providing for relative movement of each of the sheath 38, the pusher tube 36, and the inflation tube 34. In addition, the alternative embodiment employs a drive roller mechanism for translation of rotational movement of the actuator knob into axial movement of the sheath 38, pusher tube 36, and inflation tube 34.

Turning to FIG. 13A, a lower housing member 230*a* encloses a proximal bulkhead 232 and a distal bulkhead 234. A first lead screw 236, a second lead screw 238, and a third lead screw 240 extend between and are supported by the proximal bulkhead 232 and distal bulkhead 234. A paving nut 242 includes internal threads to allow axial travel along the first lead screw.

A separation nut 244 includes internal threads to allow travel along the second lead screw. A reset nut 246 includes internal threads to allow travel along the third lead screw. Although not shown in FIG. 13A, the paving nut 242 is attached to the sheath 38, the separation nut 244 is attached to the pusher tube 36, and the reset nut 246 is attached to the inflation tube 34, each in a manner similar to that described above for the first embodiment of the handle 28. Each of the first, second, and third lead screws 236, 238, 240 includes a roller receptacle 248, 250, 252 fixed to the distal end of the respective lead screw.

Figure 15:
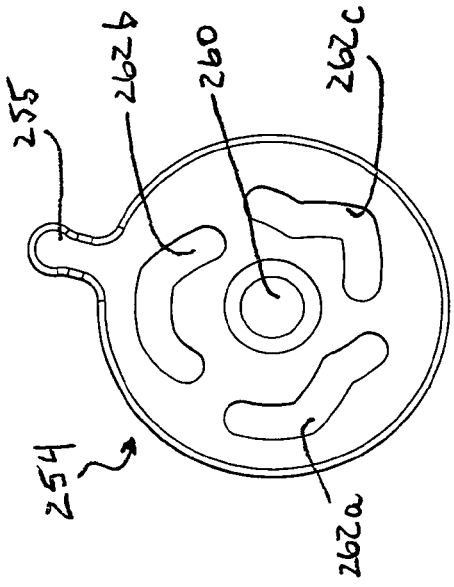
FIG. 15 shows a selector.
Figure 14:
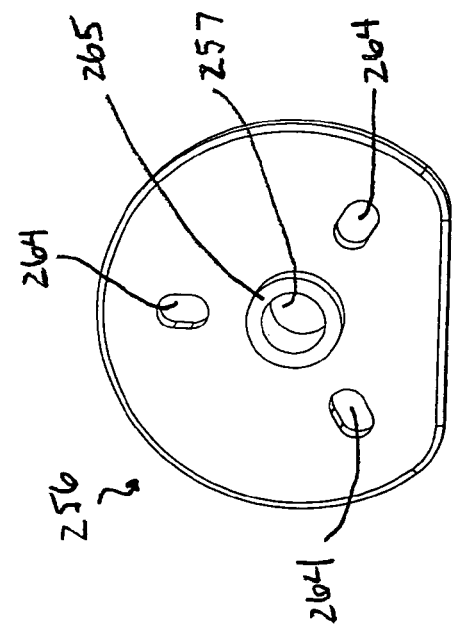
FIG. 14 shows a distal selector guide.

A selector 254 is received and retained in the housing 230*a* between a distal selector guide 256 and a proximal selector guide 258. The selector 254 is illustrated in greater detail in FIG. 15. The selector includes a lever 255, a center aperture 260, and three elongated slots 262*a-c* surrounding the center aperture 260. Each of the elongated slots 262*a-c* includes a distinct cam feature, the purpose of which is described below. The distal selector guide 256 is illustrated in greater detail in FIG. 14. The distal selector guide 256 includes a center aperture 257 and three through-holes 264 surrounding the center aperture 257. A raised brake surface 265 is located around the periphery of the center aperture 257 between the center aperture 257 and the through-holes 264.

An actuator knob 266 is provided at the distal end of the handle 28. See FIG. 13A. Three rollers 268*a-c* are enclosed within the interior of the actuator knob 266. See FIG. 13B.

Each of the rollers 268*a-c* includes a first engagement head 269*a-c* located on the distal side of the distal selector guide 256, a second engagement head 270*a-c* located on the proximal side of the proximal selector guide 258, and a shaft 271*a-c* extending between the first engagement heads and second engagement heads. The second engagement heads 270*a-c* are selectively engageable with the receptacles 248, 250, 252, while the first engagement heads 269*a-c* are selectively engageable with the actuator knob 266, as described below.

Figure 16A:
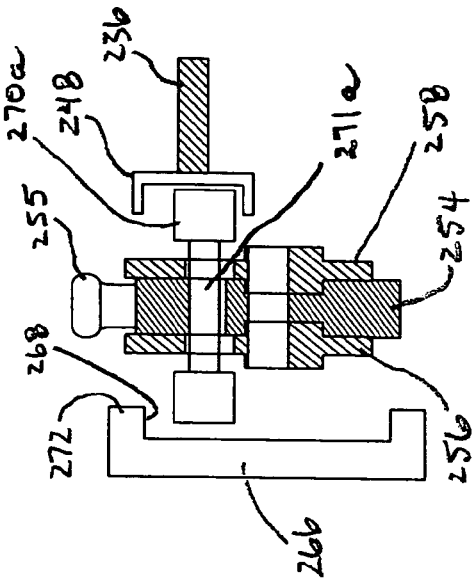
FIG. 16A is a schematic diagram showing a structure for translating rotation of an actuator knob into rotation of a lead screw.
Figure 16B:
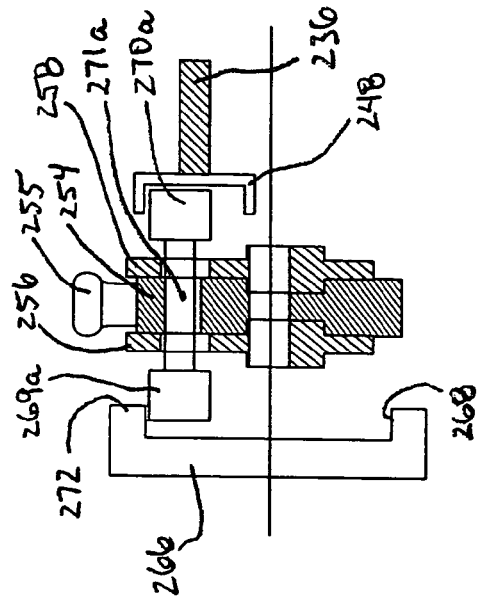
FIG. 16B is another schematic diagram of the structure shown in FIG. 16A.

Referring to FIGS. 16A and 16B, the actuator knob 266 includes an edge 267 that forms an internal engagement surface 272. The first engagement head 269*a* of the first roller 268*a* is selectively engaged with the internal engagement surface 272 of the actuator knob. Each of the other engagement heads 268*b*, 268*c* is similarly engageable with the engagement surface 272 of the actuator knob. More specifically, the shaft 271*a-c* of each of the rollers extends through one of the elongated slots 262*a-c* of the selector 254. As the selector 254 is rotated, the cam feature of each of the elongated slots 262*a-c* causes the shaft 271 a-c of the roller to move radially inward (toward the central longitudinal axis of the handle) or radially outward (away from the central longitudinal axis). When the shaft 271 *a-c* is moved radially inward, the respective first engagement head 269*a-c* disengages from the engagement surface 272 of the actuator knob 266, and comes into contact with the brake surface 265 of the distal selector guide 256. (See FIG. 16A). In this position, rotation of the actuator knob 266 does not cause rotation of the roller 268*a-c*. On the other hand, when the shaft 271*a-c* is moved radially outward, the respective first engagement head 269*a-c* engages with the engagement surface 272 of the actuator knob 266, and disengages from the brake surface 265 of the distal selector guide 256. (See FIG. 16B). In this position, rotation of the actuator knob 266 causes the respective roller 268*a-c* to rotate as well. The respective second engagement head 270*a-c* will be in contact with the respective receptacle 248, 250, 260, thereby causing rotation of the respective lead screw 236, 238, 240.

The selector 254 has three positions. In a first position, corresponding to the paving process, only the first roller 268a is biased outward by the selector to engage the actuator knob 266, while the other two rollers 268b-c are biased inward to the brake surface 265. In this position, only the first lead screw 236 is rotated, while the second and third lead screws 238, 240 remain stationary. This results in retraction of the sheath 38 while maintaining the inflation tube 34 and pusher tube 36 in place, thereby facilitating the paving process.

In a second selector position, corresponding to the separation process, both the first roller 268a and the second roller 268b are biased outward by the selector 254 to engage the actuator knob 266, while the third roller 268c is biased inward to the brake surface 265. In this position, the first lead screw 236 and second lead screw 238 are rotated, while the third lead screw 240 remains stationary. This results in retraction of the sheath 38 and pusher tube 36 while maintaining the inflation tube 34 in place, thereby facilitating the separation process.

In a third selector position, corresponding to the resetting process, both the first roller 268a and the second roller 268b are biased inward by the selector 254 to engage the brake surface 265, while the third roller 268c is biased outward to the actuator knob 266. In this position, the first lead screw 236 and second lead screw 238 remain stationary, while the third lead screw 240 rotates. This results in retraction of inflation tube 34 while maintaining the sheath 38 and the pusher tube 36 in place, thereby facilitating the resetting process.

Advantageously, each of the three processes—paving, separating, and resetting—are provided while rotating the actuator knob 266 in only a single direction.

Figure 17:
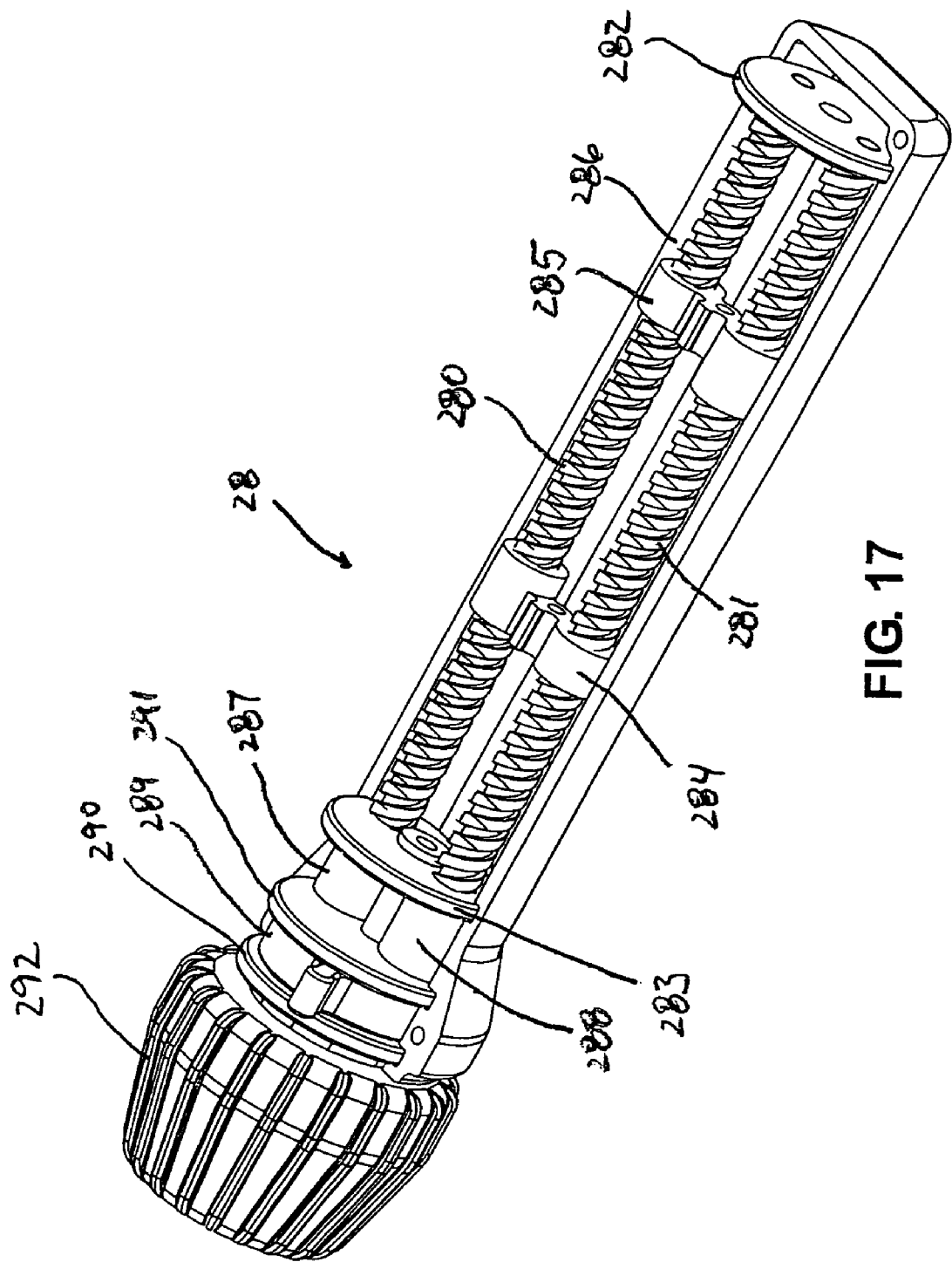
FIG. 17 shows a perspective view of another alternative embodiment of a handle member of the stent delivery catheter with the upper housing removed.
Figure 18A:
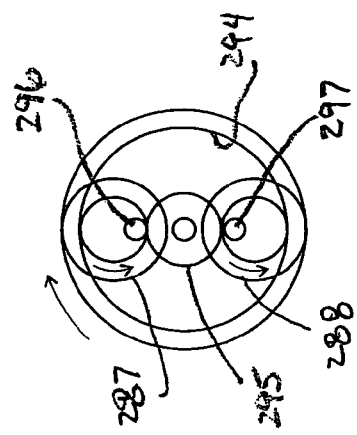
FIG. 18A is a schematic diagram showing a side view of a structure for translating rotation of an actuator knob into rotation of a lead screw.
Figure 18B:
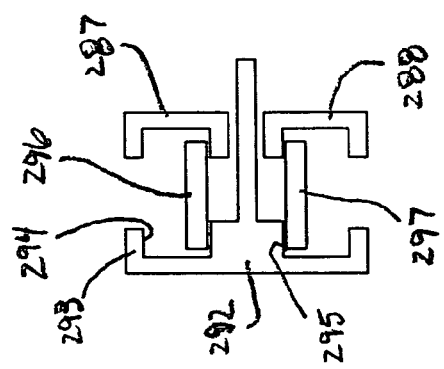
FIG. 18B is a schematic diagram showing the front view of the structure shown in FIG. 18A.
Figure 19A:
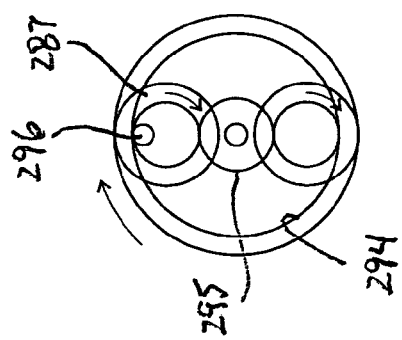
FIG. 19A is another schematic diagram of the structure shown in FIG. 18A.
Figure 19B:
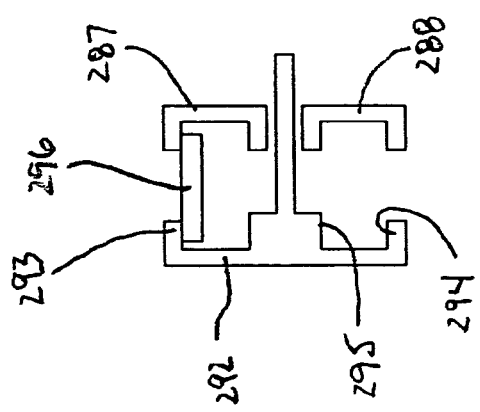
FIG. 19B is another schematic diagram of the structure shown in FIG. 18B.

Turning to FIGS. 17-19, another alternative embodiment of the handle 28 is illustrated. In this further alternative embodiment, the handle 28 includes two lead screws 280, 281 supported within a housing 286 by a proximal bulkhead 282 and a distal bulkhead 283. A threaded paving nut 284 is adapted to travel on the first lead screw 280, and a threaded separation nut 285 is adapted to travel on the second lead screw 281. Although not shown in FIG. 17, the paving nut 284 is attached to the sheath 38, and the separation nut 285 is attached to the pusher tube 36, in a manner similar to that described above in relation to the other handle embodiments.

A first receptacle 287 is fixed to the distal end of the first lead screw 280, and a second receptacle 288 is fixed to the distal end of the second lead screw 281. A selector 289 is located between a distal selector guide 290 and a proximal selector guide 291. An actuator knob 292 is rotatably attached to the distal end of the handle 28. The actuator knob 292 includes an outer edge 293 that forms an outer engagement surface 294, and a central hub 295 that forms an inner engagement surface. (See FIGS. 18A-B, 19A-B).

A first roller 296 extends between the first receptacle 287 and the actuator knob 292, and a second roller 297 extends between the second receptacle 288 and the actuator knob 292. The first roller 296 and second roller 297 are subject to being moved radially inward and outward by rotation of the selector 289, in a manner similar to that described above in relation to the preceding embodiment. For example, in FIGS. 18A and 18B, the first roller 296 is biased radially outward such that it engages the outer engagement surface 294 of the actuator knob 292, and the upper surface of the first receptacle 287. In this position, counter-clockwise rotation of the actuator knob 292 produces counter-clockwise rotation of the first receptacle 287 and, hence, counterclockwise rotation of the first lead screw 280. On the other hand, in FIGS. 19A and 19B, the first roller 296 is biased radially inward such that it engages the hub 295 of the actuator knob 292, and the lower surface of the first receptacle 287. In this position, counter-clockwise rotation of the actuator knob 292 produces clockwise rotation of the first receptacle 287 and, hence, clockwise rotation of the first lead screw 280.

Thus, adjusting the position of the first roller 296 and second roller 297 by rotating the selector 289 will provide any desired combination of advancing and retracting movement of the sheath 38 and the pusher tube 36 while rotating the actuator knob 292 in only a single direction. Preferably, the selector 289 is provided with three positions. A first position, corresponding to the paving process, includes having the first roller 296 in contact with the outer engagement surface 294 of the actuator knob, while the second roller 297 is not engaged with any portion of the actuator knob 292. Rotation of the actuator knob 292 causes the sheath 38 to be retracted. A second position, corresponding with the separation process, includes having both the first roller 296 and the second roller 297 in contact with the outer engagement surface 294 of the actuator knob. Rotation of the actuator knob 292 causes both the sheath 38 and the pusher tube 36 to retract. Finally, a third position, corresponding with the resetting process, includes having both the first roller 296 and the second roller 297 in contact with the hub 295. Rotation of the actuator knob 292 causes both the sheath 38 and the pusher tube 36 to advance. In each case, the actuator knob 292 is rotated in the same direction to perform the process.

The various devices described herein are suitable for use in any suitable apparatus, device, system, or method in which relative longitudinal motion of two or more device components is desired. The devices are able to be applied to any number of components by providing an appropriate number of lead screws. The devices employ a beneficially economic design that provides single-handed actuation of both the selector and the actuator knob, and that includes selector and actuator knob rotation around the same longitudinal axis. The design allows manipulation of the actuator with the thumb and forefinger while gripping the device with the other fingers. The device is preferably compact, streamlined, and does not include any substantially protruding parts or features. The device may be readily motorized by incorporating a servomotor in place of the actuator knob. In addition, one or more sensors or other signaling mechanisms may be incorporated in the catheter shaft to provide feedback concerning the precise position of the interventional element during the paving, separation, and/or resetting processes.

The preferred embodiments of the inventions that are the subject of this application are described above in detail for the purpose of setting forth a complete disclosure and for the sake of explanation and clarity. Those skilled in the art will envision other modifications within the scope and spirit of the present disclosure. Such alternatives, additions, modifications, and improvements may be made without departing from the scope of the present inventions, which is defined by the claims.

What is claimed is:

1. A catheter comprising:
   an elongated catheter shaft having a distal end and a proximal end and further comprising an inner shaft and an outer shaft, said outer shaft being slidably disposed over said inner shaft;
   an interventional element at the distal end of the catheter shaft, the interventional element having an adjustable length;
   an actuator attached to the proximal end of the catheter shaft for adjusting the length of the interventional element, said actuator having a longitudinal axis and including at least one lead screw configured to operatively couple a rotatable member to the catheter shaft, said rotatable member being rotatable around the longitudinal axis of the actuator;

at least one threaded member configured to operatively couple said at least one lead screw and said catheter shaft, said at least one threaded member configured to travel axially along said at least one lead screw as the at least one lead screw rotates;

a first threaded member configured to operatively couple a first lead screw to said outer shaft, said first threaded member configured to travel axially along said first lead screw as the first lead screw rotates, and a second threaded member configured to operatively couple a second lead screw to said inner shaft, said second threaded member configured to travel axially along said second lead screw as the at second lead screw rotates.

2. The catheter of claim 1, further comprising at least one gear member configured to operatively couple said rotatable member and said at least one lead screw such that rotation of said rotatable member causes rotation or said at least one lead screw.

3. The catheter of claim 1, further comprising at least one roller member configured to operatively couple said rotatable member and said at least one lead screw such that rotation of said rotatable member causes rotation of said at least one lead screw.

4. The catheter of claim 1, further comprising
at least two lead screws configured to operatively couple said rotatable member to said catheter shaft, and
a selector having a first setting in which a first of said at least two lead screws operatively couples said rotatable member to said catheter shaft, and a second setting in which a second of said at least two lead screws operatively couples said rotatable member to said catheter shaft.

5. The catheter of claim 4, wherein said selector is rotatably coupled to said actuator, said selector being rotatable around the longitudinal axis of the actuator.

6. The catheter of claim 5, wherein said first of said at least two lead screw operatively couples said rotatable member to said catheter shaft when the selector is at its second setting.

7. The catheter of claim 4, further comprising a first gear member configured to operatively couple said rotatable member and said first lead screw such that rotation of said rotatable member causes rotation of said first lead screw.

* * * * *